(12) United States Patent
Miki et al.

(10) Patent No.: US 8,247,087 B2
(45) Date of Patent: Aug. 21, 2012

(54) COMPOUND HAVING OXADIAZOLE RING STRUCTURE BONDED WITH AROMATIC HETEROCYCLIC RING AND ORGANIC ELECTROLUMINESCENT DEVICE

(75) Inventors: Tetsuzo Miki, Minato-ku (JP); Norimasa Yokoyama, Tsukuba (JP); Shuichi Hayashi, Tsukuba (JP); Shigeru Kusano, Tsukuba (JP); Yoshio Taniguchi, Ueda (JP); Musubu Ichikawa, Ueda (JP)

(73) Assignees: Hodogaya Chemical Co., Ltd., Tokyo (JP); Shinshu University, Matsumoto-shi (JP)

( * ) Notice: Subject to any disclaimer, the term of this patent is extended or adjusted under 35 U.S.C. 154(b) by 561 days.

(21) Appl. No.: 12/066,508

(22) PCT Filed: Sep. 12, 2006

(86) PCT No.: PCT/JP2006/318082
§ 371 (c)(1),
(2), (4) Date: Mar. 12, 2008

(87) PCT Pub. No.: WO2007/032357
PCT Pub. Date: Mar. 22, 2007

(65) Prior Publication Data
US 2009/0230849 A1     Sep. 17, 2009

(30) Foreign Application Priority Data
Sep. 12, 2005  (JP) ................... 2005-263687

(51) Int. Cl.
*H01L 51/54* (2006.01)
(52) U.S. Cl. ........ 428/690; 428/917; 313/504; 313/505; 313/506; 257/40; 257/E51.05; 548/440
(58) Field of Classification Search .......... 428/690, 428/917; 313/504, 505, 506; 257/40, E51.05; 548/440
See application file for complete search history.

(56) References Cited

U.S. PATENT DOCUMENTS

| | | | | |
|---|---|---|---|---|
| 3,600,383 | A | * | 8/1971 | Atkinson et al. ............ 548/143 |
| 5,378,519 | A | * | 1/1995 | Kikuchi et al. ............ 428/690 |
| 5,702,833 | A | * | 12/1997 | Nagai et al. ............ 428/690 |
| 2003/0168970 | A1 | * | 9/2003 | Tominaga et al. ............ 313/504 |
| 2005/0146263 | A1 | * | 7/2005 | Kelly et al. ............ 313/504 |

FOREIGN PATENT DOCUMENTS

| | | | |
|---|---|---|---|
| DE | 25 09 514 | | 9/1976 |
| EP | 1 607 392 A1 | | 12/2005 |
| FR | 1 473 521 | | 3/1967 |
| GB | 1543368 | * | 4/1979 |
| JP | 05-255664 | * | 10/1993 |
| JP | 07-109454 | * | 10/1993 |
| JP | 7 109454 | | 4/1995 |
| JP | 8 3148 | | 1/1996 |
| JP | 8 3150 | | 1/1996 |
| JP | 8 48656 | | 2/1996 |
| JP | 8 176148 | | 7/1996 |
| JP | 3194657 | | 6/2001 |
| WO | WO 2004/083194 A1 | | 9/2004 |
| WO | 2005 092888 | | 10/2005 |

OTHER PUBLICATIONS

English Translation of JP 07-109454.*
Wu et. al., Organic Electroluminescent device . . . carrier injection and transportation, 2000, Thin Solid Films, vol. 363, pp. 214-217.*
Miki et al., Bipyridyl Oxadiazoles as a New class of Durable and Efficient Electron-Transporting Materails, 2005, SID Symposium Digest of Technical Papers, vol. 36, pp. 1652-1655.*
Ichikawa, M, et al., "Bipyridyl Oxadiazoles as a New Class of Durable and Efficient Electron-Transporting Materials", Digest of Technical Papers, Society for Information Display International Symposium, vol. 36, pp. 1652-1655, 2005.
Belen'Kii, L.I. et al., "Novel Syntheses of Symmetrical 2,5-Diaryl-1,3,4-Oxadiazoles and 1,4-Phenylenebis-1,3,4-Oxadiazoles" Russian Chemical Bulletin, vol. 47, No. 11, pp. 2238-2245, 1998.
Hergenrother, P.M., "1,2,4-Triazoles and 1,3,4-Oxadiazoles From N-Acylhydrazines," Journal of Heterocyclic Chemistry, Chemical Abstracts, vol. 72 p. 450, 1970.
Patsenker, L.D. et al., "Spectral and Quantum-Chemical Study of Some 1,4-Bis (5-Phenylazolyl-2) Benzene Heteroanalogs, Khimiya Geterotsiklicheskikh Soedinenii," vol. 6, pp. 817-821, 1991.
Chishio Hosokawa, et al., Preprints for 91$^{th}$ Workshop of Japan Applied Physics, 2001, pp. 55-61.

(Continued)

*Primary Examiner* — Jennifer Chriss
*Assistant Examiner* — Gregory Clark
(74) *Attorney, Agent, or Firm* — Oblon, Spivak, McClelland, Maier & Neustadt, L.L.P.

(57) ABSTRACT

An object of the invention is to provide an organic compound having excellent characteristics as a material for highly efficient and highly durable organic EL devices, and also to provide a highly efficient and highly durable organic EL device. This invention relates to a compound represented by the general formula (1) having an oxadiazole ring structure bonded with an aromatic heterocycle, and to an organic electroluminescence device containing the compound:

[Chem. 1]

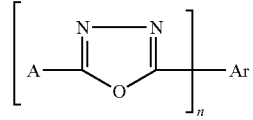

(1)

wherein Ar represents a substituted or unsubstituted aromatic hydrocarbon group, a substituted or unsubstituted aromatic heterocyclic group, or a substituted or unsubstituted condensed polycyclic aromatic group; A represents a substituted or unsubstituted aromatic heterocyclic group; and n represents an integer of 1 to 3.

20 Claims, 5 Drawing Sheets

OTHER PUBLICATIONS

Takeo Wakimoto, "Optimization of driving lifetime durability in organic LED devices using phosphorescent guest emitter", Preprints for 9th Workshop of Japan Applied Physics, 2001, pp. 23-31.

Chihaya Adachi, et al., "Electroluminescence in Organic Films with Three-Layer Structure", Japanese Journal of Applied Physics, vol. 27, No. 2, Feb. 1988, pp. L269-L271.

European Office Action issued Mar. 23, 2012 in patent application No. 06 797 874.2.

Jürgen Sauer, et al., "3,6-Bis(2H-tetrazol-5-yl)-1,2,4,5-tetrazine: A Versatile Bifunctional Building Block for the Synthesis of Linear Oligoheterocycles", European Journal of Organic Chemistry, XP55021334, Jan. 22, 2001, pp. 697-706.

* cited by examiner

COMPOUND HAVING OXADIAZOLE RING STRUCTURE BONDED WITH AROMATIC HETEROCYCLIC RING AND ORGANIC ELECTROLUMINESCENT DEVICE

TECHNICAL FIELD

This invention relates to a compound and a device suitable for an organic electroluminescence (EL) device which is a self-luminescent device suitable for various display apparatuses and to a device. More specifically, the invention relates to a compound having an oxadiazole ring structure bonded with an aromatic heterocycle and to an organic EL device using the compound.

BACKGROUND ART

Since the organic EL devices are self-luminescent devices, they are bright, excellent in visibility, and capable of giving clear display as compared to liquid crystal devices, and studies thereon have actively been conducted.

In 1987, C. W. Tang et al. of Eastman Kodak Co. have turned an organic EL device using an organic material into practical utilization by developing a multilayered structure device wherein various functions are respectively distributed to materials. They stack a fluorescent material capable of transporting electrons and an organic substance capable of transporting holes, and injected both of the charges into the fluorescent material layer to emit a light, thereby achieving a high luminance of 1,000 cd/m$^2$ or more at a voltage of 10 V or less (see Patent Document 1 and Patent Document 2, for example).

Patent Document 1: JP-A-8-48656
Patent Document 2: Japanese Patent No. 3194657

Many improvements have been made up to the present for putting organic EL devices into practical use, and high efficiency and durability have been achieved by an electroluminescence device wherein an anode, a hole injection layer, a hole transport layer, an emitting layer, an electron transport layer, an electron injection layer, and a cathode are provided in this order on a substrate, thereby further segmentalizing various roles (see Non-Patent Document 1, for example).

Non-Patent Document 1: Preprints for 9th Workshop of Japan Applied Physics, pages 55 to 61 (2001)

Also, there has been an attempt for utilizing a triplet exciton in the aim of a further improvement in luminescent efficiency, and use of phosphorescent materials has been studied (see Non-Patent Document 2, for example).

Non-Patent Document 2: Preprints for 9th Workshop of Japan Applied Physics, pages 23 to 31 (2001)

The emitting layer may be produced by doping a compound having carrier transport property, which is generally called a host material, with a fluorescent material or phosphorescent material. As disclosed in the above-mentioned workshop preprints, selection of an organic material in an organic EL device greatly influences on various properties of the device, such as efficiency and durability.

In organic EL devices, luminescence is obtained when charges injected from the electrodes are re-combined in the emitting layer. Since the transfer rate of holes is higher than that of the electrons, a problem of reduction in efficiency caused by a part of holes passing through the emitting layer arises. Therefore, an electron transport material enabling easy electron transfer has been demanded.

Although tris(8-hydroxyquinoline)aluminum (hereinafter abbreviated as Alq) which is a typical luminous material is also generally used as an electron transport material, the electron mobility thereof is considered to be low. Therefore, as a material having a high electron mobility, 2-(4-biphenylyl)-5-(4-t-butylphenyl)-1,3,4-oxadiazole (hereinafter abbreviated as PBD) and the like have been proposed (see Non-Patent Document 3, for example).

Non-Patent Document 3: Jpn. J. Appl. Phys., 27, L269 (1988)

However, it has been pointed out that PBD has poor stability in its thin film state, such as readily undergoing crystallization, and no satisfactory device property has been achieved.

DISCLOSURE OF THE INVENTION

Problems to be Solved by the Invention

An object of this invention is to provide an organic compound having excellent properties as a material for organic EL devices, such as enabling easy electron transfer and having high stability in a thin film state, and also to provide an organic EL device having good efficiency and durability by using the compound.

Means to Solve the Problems

In order to attain the above objects, the inventors designed and chemically synthesized novel organic compounds in which an aromatic heterocycle is bonded to an oxadiazole ring, experimentally produced various organic EL devices by using the compounds, and conducting characteristics evaluations of the devices, thereby accomplishing this invention.

That is, this invention provides a compound represented by the general formula (1) comprising an oxadiazole ring structure bonded with an aromatic heterocycle:

[Chem. 1]

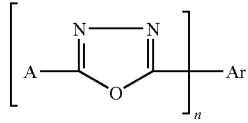

wherein Ar represents a substituted or unsubstituted aromatic hydrocarbon group, a substituted or unsubstituted aromatic heterocyclic group, or a substituted or unsubstituted condensed polycyclic aromatic group; A represents a substituted or unsubstituted aromatic heterocyclic group; and n represents an integer of 1 to 3.

Also, this invention provides an organic EL device comprising a pair of electrodes and at least one organic layer sandwiched therebetween, comprising the compound as a constituting material of the at least one organic layer.

Specific examples of the aromatic hydrocarbon group, the aromatic heterocyclic group, or the condensed polycyclic aromatic group in the substituted or unsubstituted aromatic hydrocarbon group, the substituted or unsubstituted aromatic heterocyclic group, or the substituted or unsubstituted condensed polycyclic aromatic group represented by Ar in the general formula (1) include a phenyl group, a biphenyl group, a terphenyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyronyl group, a thiophenyl group, a quinolyl group, a benzofuranyl group, a benzothiophenyl group, an indolyl group, a carbazolyl group, a benzooxazolyl group, a quinoxalyl group, a benzoimidazolyl group, a pyrazolyl group, a dibenzofuranyl group, a dibenzothiophenyl group, and the like.

Specific examples of the substituent group in the substituted aromatic hydrocarbon group, the substituted aromatic heterocyclic group, or the substituted condensed polycyclic aromatic group represented by Ar in the general formula (1) include a fluorine atom, a chlorine atom, a cyano group, a hydroxide group, a nitro group, an alkyl group, an alkoxy group, an amino group, a substituted amino group, a trifluoromethyl group, a phenyl group, a naphthyl group, an aralkyl group, a phenyl group having a substituted group, a naphthyl group having a substituted group, an aralkyl group having a substituted group, and the like.

Specific examples of the substituted or unsubstituted aromatic heterocyclic group represented by A in the general formula (1) include a phenanthryl group, a pyronyl group, a furanyl group, a pyrazolyl group, an oxazolyl group, a thiazolyl group, a pyrimidyl group, a triazyl group, a thiophenyl group, a quinolyl group, a quinoxalyl group, a benzofuranyl group, a benzothiophenyl group, a benzooxazolyl group, a benzothiazolyl group, a benzoimidazolyl group, a dibenzofuranyl group, a dibenzothiophenyl group, a carbazolyl group, an indolyl group, an indenyl group, a pyrenyl group, and the like.

Specific examples of the substituent group in the substituted aromatic heterocyclic group represented by A in the general formula (1) include a fluorine atom, a chlorine atom, a cyano group, a hydroxide group, a nitro group, an alkyl group, an alkoxy group, an amino group, a substituted amino group, a trifluoromethyl group, a phenyl group, a tolyl group, a naphthyl group, an aralkyl group, a phenyl group having a substituted group, a naphthyl group having a substituted group, and the like.

The compound represented by general formula (1) having an oxadiazole ring structure bonded with an aromatic heterocycle enables easy electron transfer and is stable in a thin film state.

The compound of this invention represented by the general formula (1) and having an oxadiazole ring structure bonded with an aromatic heterocycle may be used as a constituting material of an electron transport layer of an organic EL device. By using the material enabling easy electron transfer as compared to a conventional material, an effect of increasing luminance of luminescence at the same driving voltage and an effect of improving durability of the organic EL device are obtained.

The compound of this invention represented by the general formula (1) and having an oxadiazole ring structure bonded with an aromatic heterocycle may be used as a constituting material of a hole blocking layer of an organic EL device.

Also, the compound of this invention represented by the general formula (1) and having an oxadiazole ring structure bonded with an aromatic heterocycle may be used as a constituting material of an emitting layer of an organic EL device.

Since the organic EL device of this invention uses the compound having an oxadiazole ring structure bonded with an aromatic heterocycle, which provides rapid electron transfer and stable thin film state, it becomes possible to realize an increase in luminance of luminescence and enhancement of durability.

Advantage of the Invention

This invention relates to a compound having an oxadiazole ring structure bonded with an aromatic heterocycle, which is useful as a constituting material of an electron transport layer, a hole blocking layer, or an emitting layer of an organic EL device, and also relates to an organic EL device produced by using the compound. By this invention, it becomes possible to reduce a driving voltage and to enhance durability of conventional organic EL devices.

DESCRIPTION OF REFERENCE NUMERALS AND SIGNS

Figure 1:
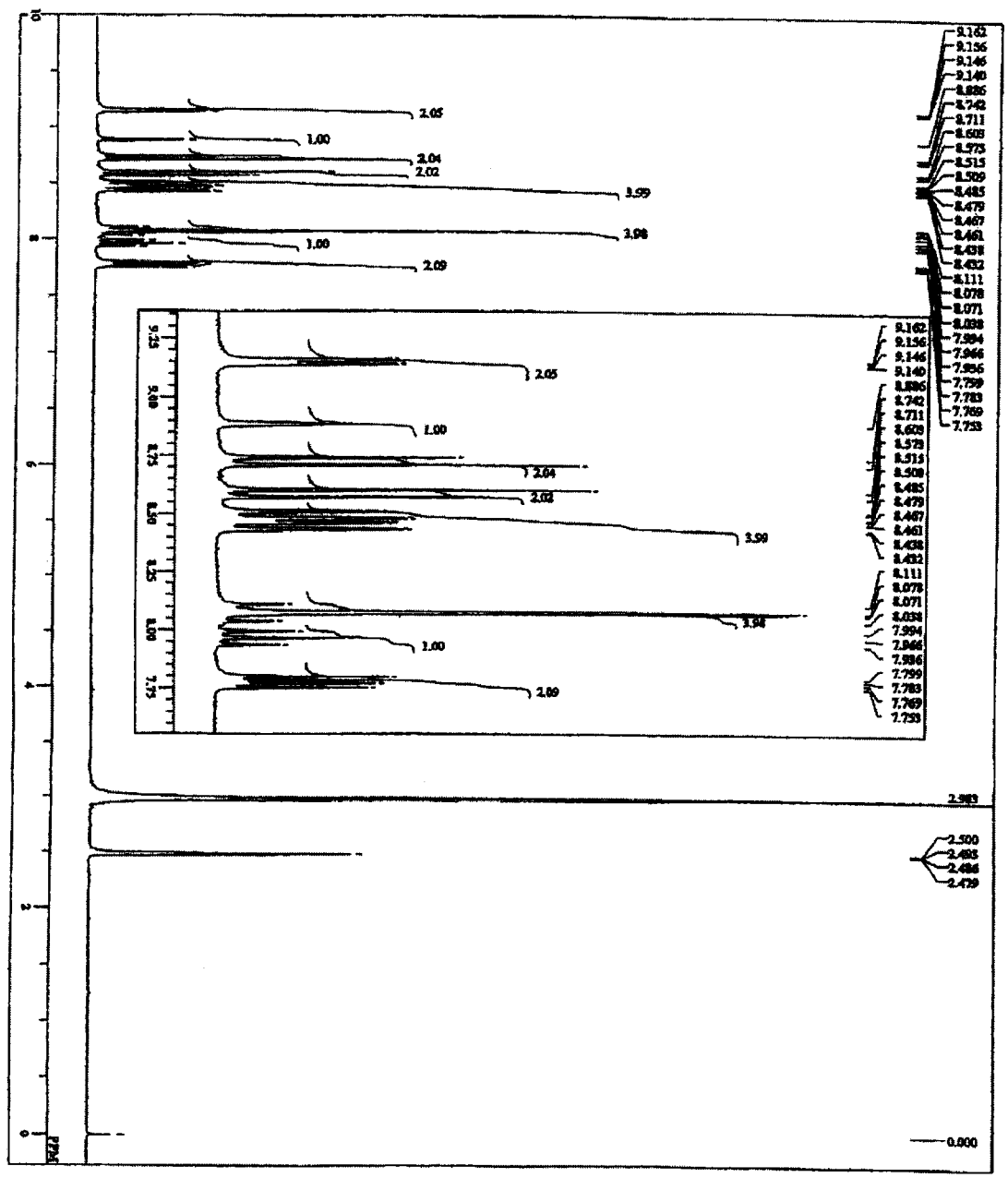
FIG. 1 is a 1H-NMR chart of PhenOXDm.

1: Glass substrate
2: Transparent anode
3: Hole injection layer
4: Hole transport layer
5: Emitting layer
6: Hole blocking layer-cum-electron transport layer
7: Electron injection layer
8: Cathode

BEST MODE FOR CARRYING OUT THE INVENTION

The compounds having an oxadiazole ring structure bonded with an aromatic heterocycle according to the invention are novel compounds, and these compounds can be synthesized, for example, by condensing various tetrazole derivatives of aromatic heterocycles with various aromatic acid chlorides (see Patent Document 3 and Non-Patent Documents 4 to 7, for example). The various tetrazole derivatives of aromatic heterocycles can be synthesized, for example, by tetrazolation using a corresponding aromatic heterocyclic nitrile compound as a raw material (see Patent Document 3 and Non-Patent Document 8, for example). Various aromatic heterocyclic nitrile compounds can be derived, for example, from a corresponding carboxylic acid (see Non-Patent Documents 9 and 10, for example), or can be synthesized by nitrilation after halogenation (see Patent Document 4, for example) or by direct nitrilation (see Non-Patent Documents 11 and 12, for example). Alternatively, commercially available products may be used. Each of the various aromatic acid chlorides may be derived, for example, from a corresponding aromatic carboxylic acid. Alternatively, commercially available products may be used.

Patent Document 3: Japanese Patent No. 3520880
Patent Document 4: JP-A-2004-175691
Non-Patent Document 4: Angew, Chem., 72, 366 (1960)
Non-Patent Document 5: Chem., Ber., 93, 2106 (1960)
Non-Patent Document 6: Tetrahedron, 11, 241 (1960)
Non-Patent Document 7: Chem., Ber., 98, 2966 (1965)
Non-Patent Document 8: Synthesis, 71 (1973)
Non-Patent Document 9: Jikken Kagaku Kouza 20 (4th edition, edited by The Chemical Society of Japan), pages 437 to 471
Non-Patent Document 10: Jikken Kagaku Kouza 22 (4th edition, edited by The Chemical Society of Japan), pages 137 to 173
Non-Patent Document 11: J. Heterocyclic Chem., 23, 989 (1986)
Non-Patent Document 12: J. Org. Chem., 30, 288 (1965)

Specific examples of preferred compounds among the compounds represented by the general formula (1) having an oxadiazole ring structure bonded with an aromatic heterocycle are shown below, but this invention is not limited to the compounds.

[Chem. 2]
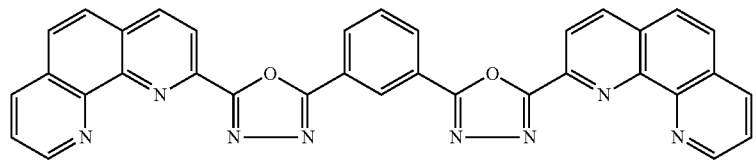
(2)
[Chem. 3]
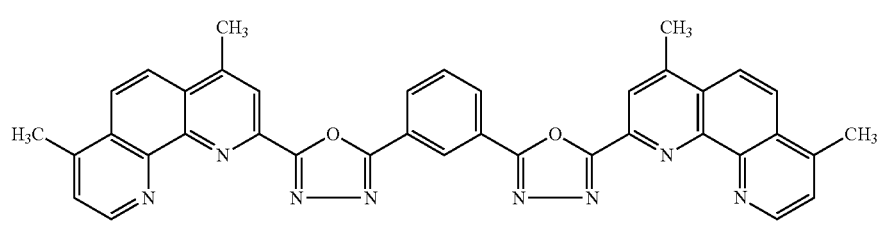
(3)
[Chem. 4]
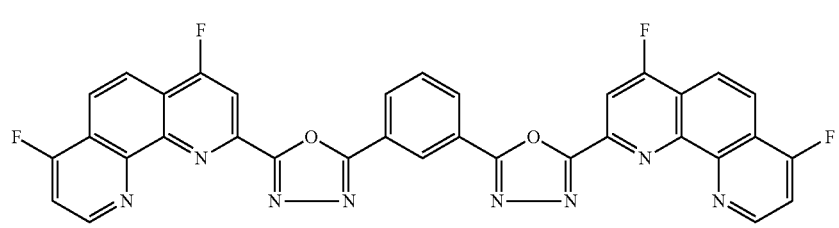
(4)
[Chem. 5]
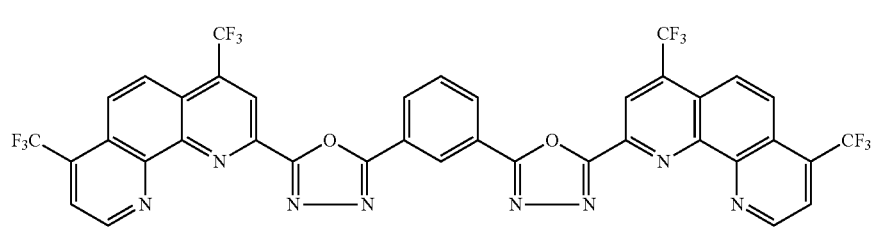
(5)
[Chem. 6]
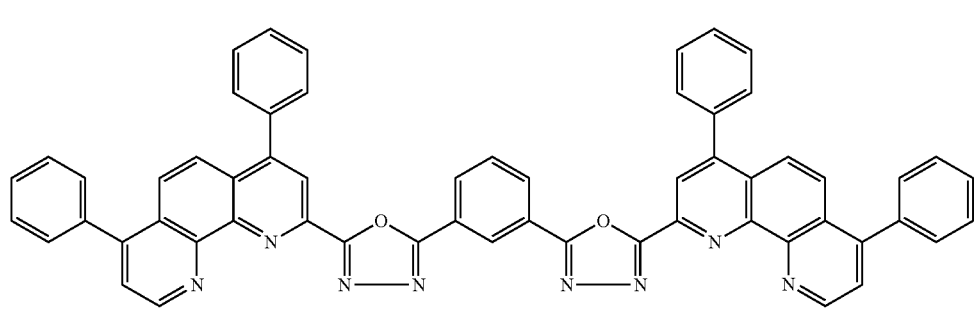
(6)
[Chem. 7]
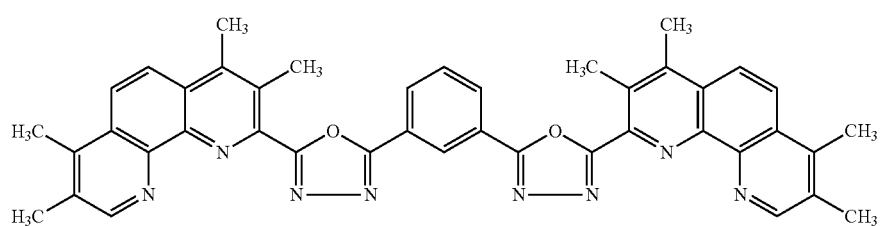
(7)

-continued
[Chem. 8]
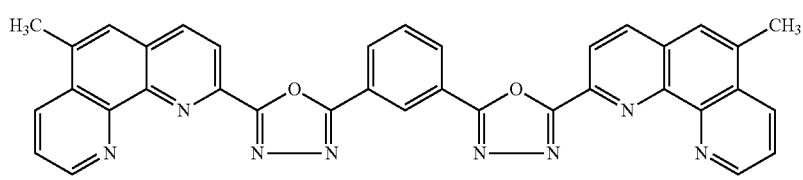
(8)
[Chem. 9]
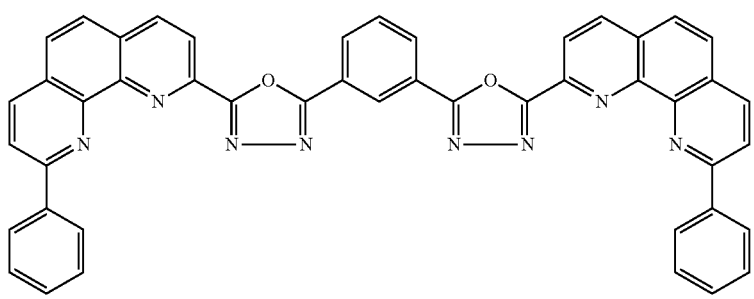
(9)
[Chem. 10]
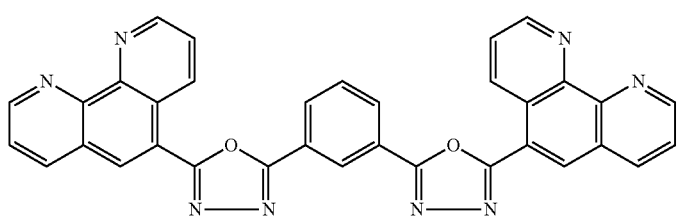
(10)
[Chem. 11]
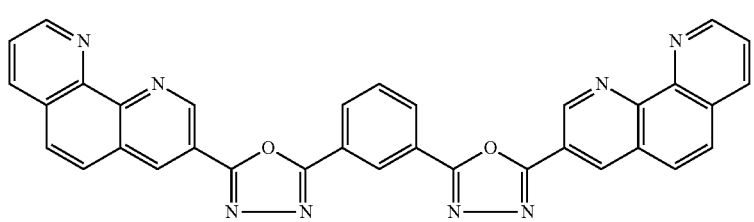
(11)
[Chem. 12]
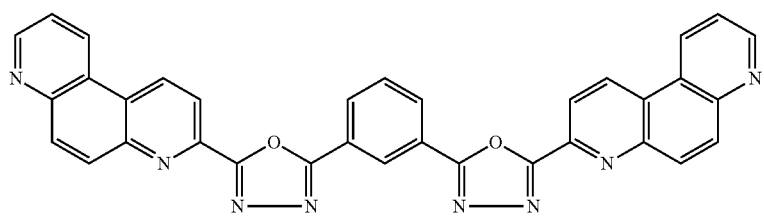
(12)
[Chem. 13]
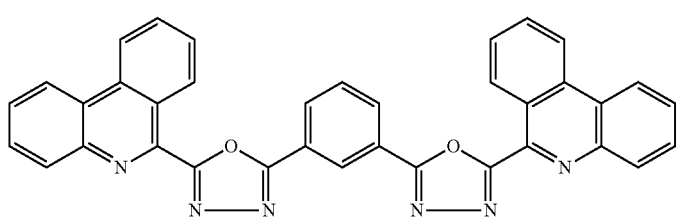
(13)

-continued
[Chem. 14]
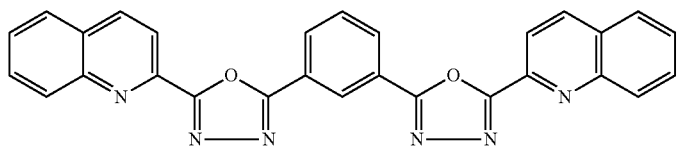
(14)
[Chem. 15]
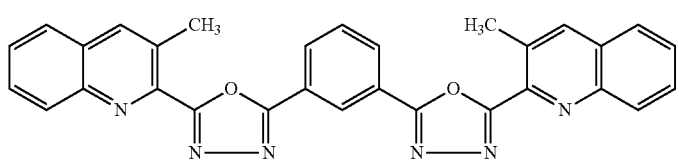
(15)
[Chem. 16]
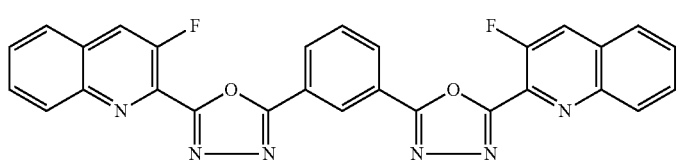
(16)
[Chem. 17]
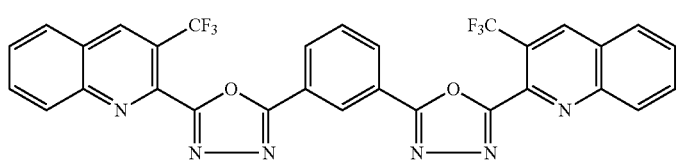
(17)
[Chem. 18]
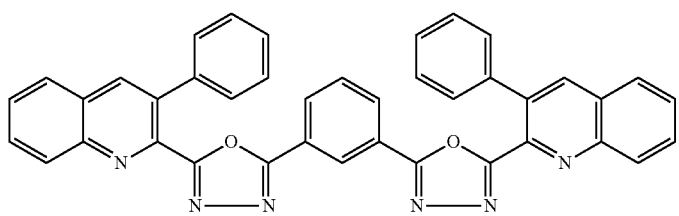
(18)
[Chem. 19]
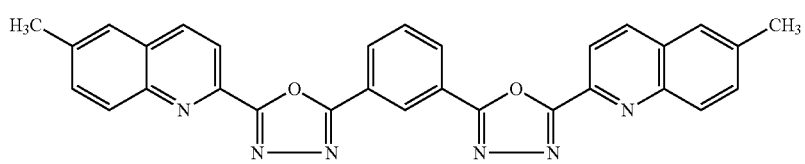
(19)
[Chem. 20]
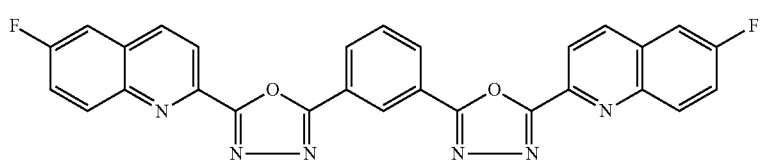
(20)

-continued
[Chem. 21]
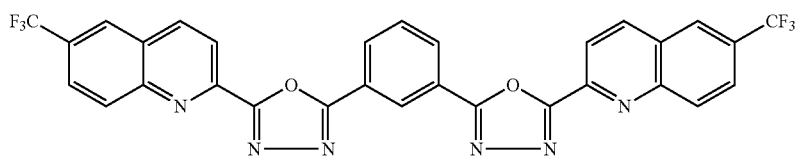
(21)
[Chem. 22]
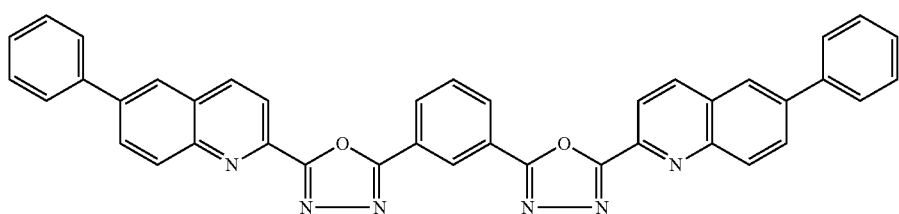
(22)
[Chem. 23]
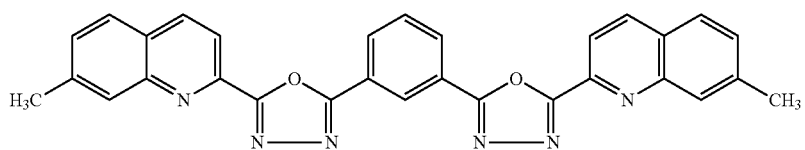
(23)
[Chem. 24]
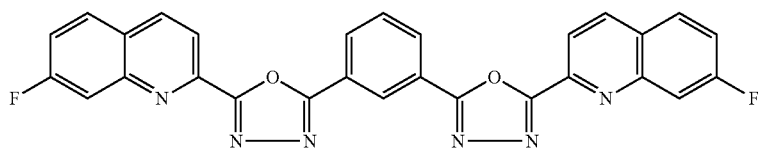
(24)
[Chem. 25]
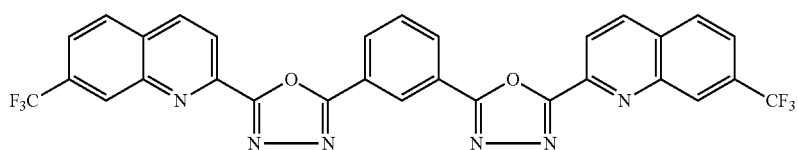
(25)
[Chem. 26]
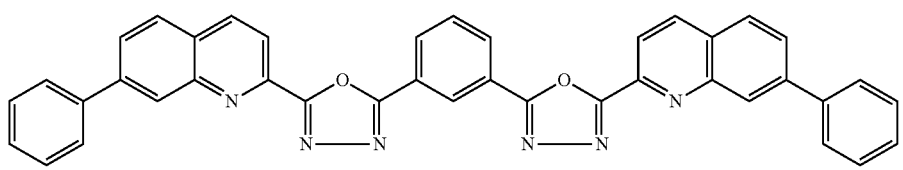
(26)
[Chem. 27]
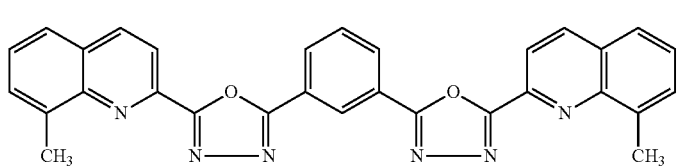
(27)
[Chem. 28]
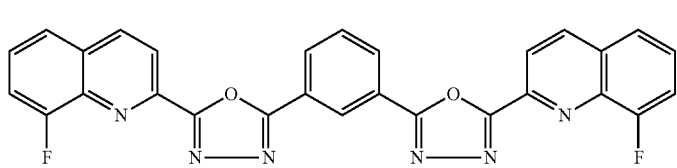
(28)

-continued
[Chem. 29]
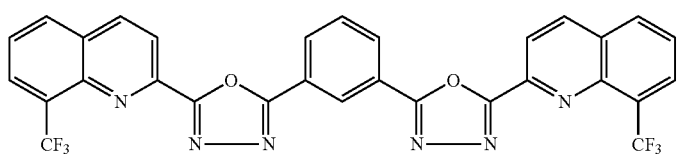
(29)
[Chem. 30]
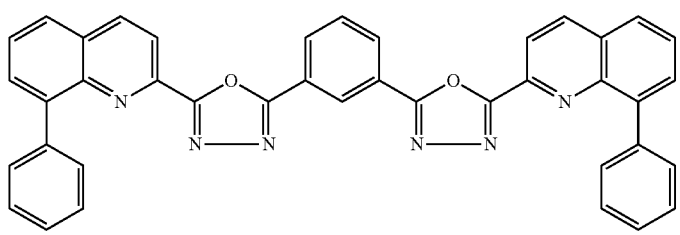
(30)
[Chem. 31]
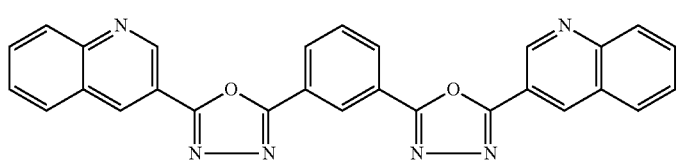
(31)
[Chem. 32]
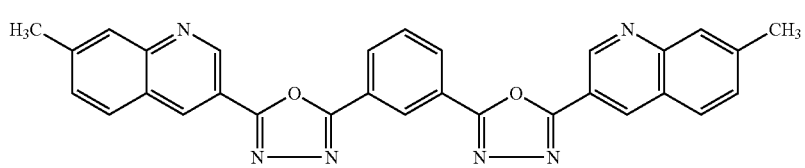
(32)
[Chem. 33]
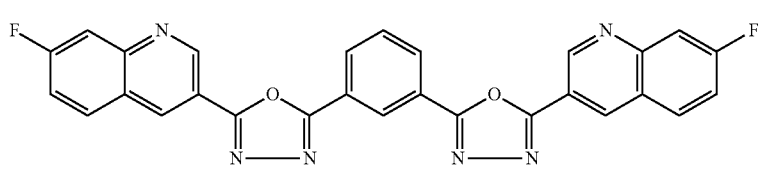
(33)
[Chem. 34]
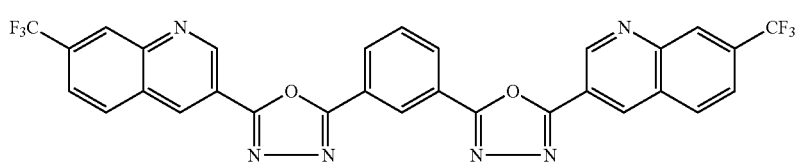
(34)
[Chem. 35]
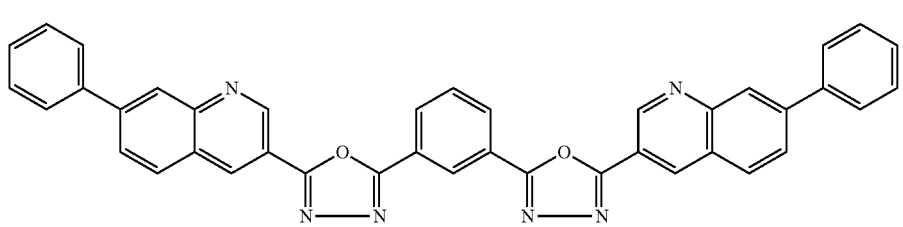
(35)

[Chem. 36]
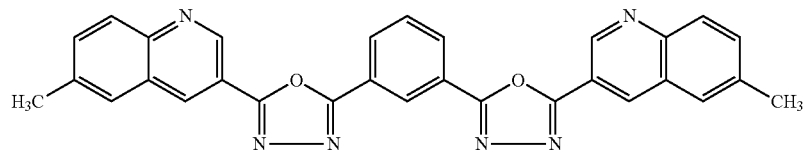
(36)
[Chem. 37]
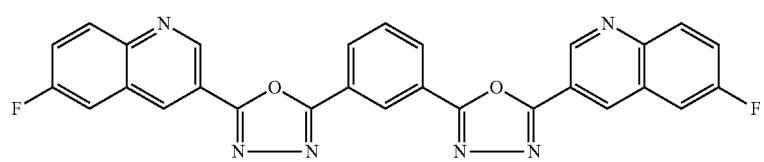
(37)
[Chem. 38]
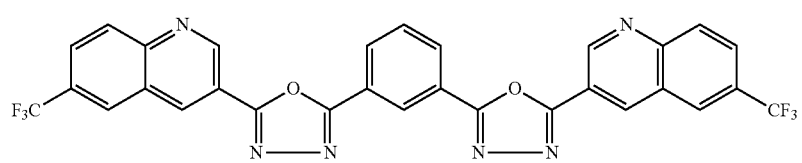
(38)
[Chem. 39]
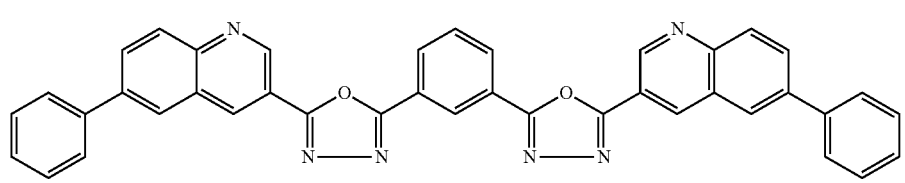
(39)
[Chem. 40]
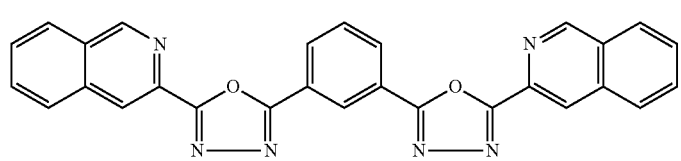
(40)
[Chem. 41]
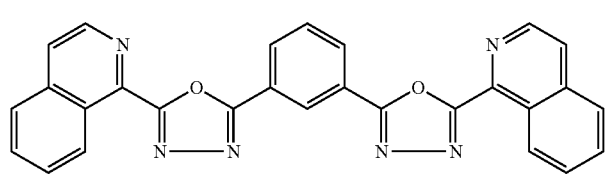
(41)
[Chem. 42]
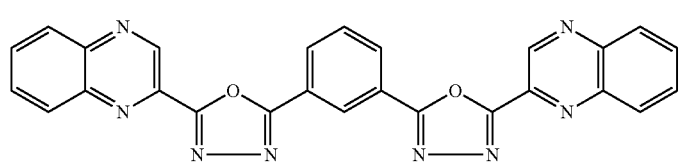
(42)

-continued
[Chem. 43]
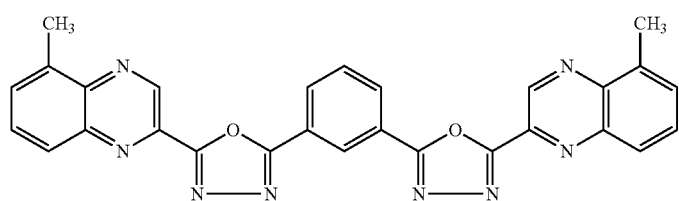
(43)
[Chem. 44]
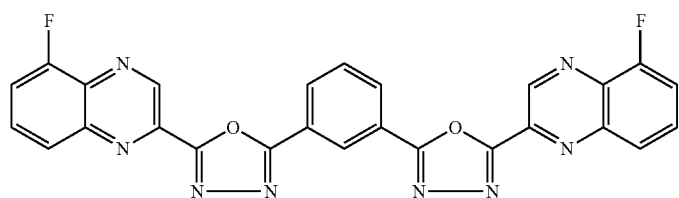
(44)
[Chem. 45]
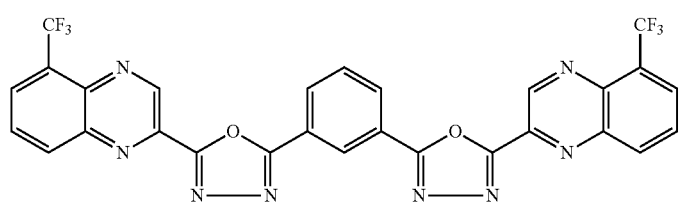
(45)
[Chem. 46]
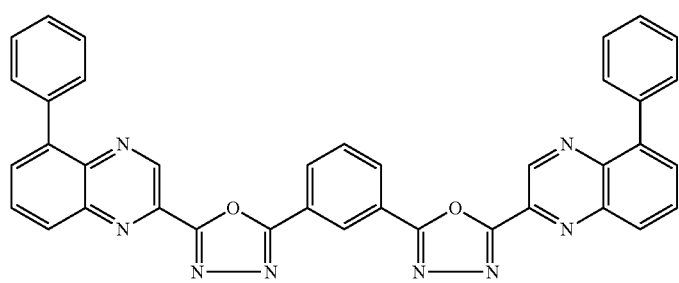
(46)
[Chem. 47]
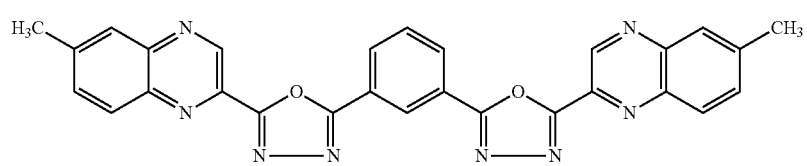
(47)
[Chem. 48]
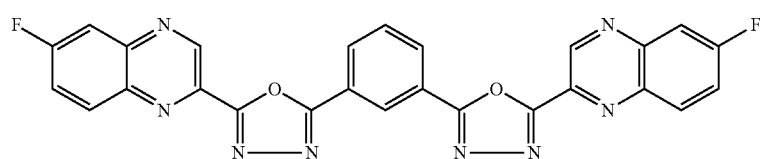
(48)
[Chem. 49]
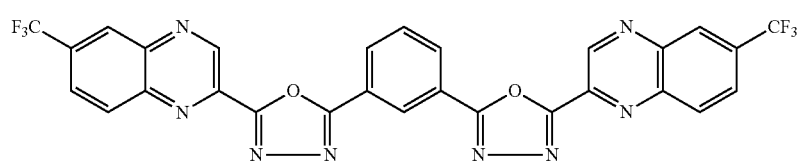
(49)

[Chem. 50]
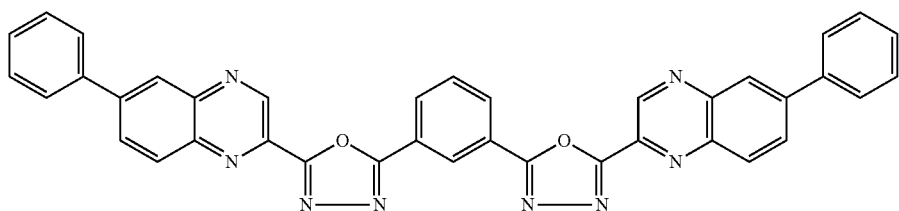
(50)
[Chem. 51]
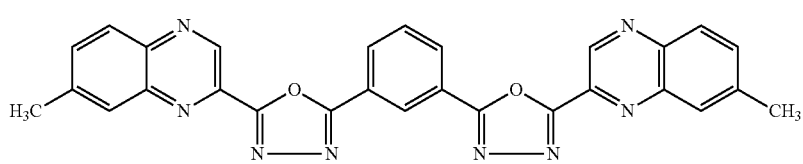
(51)
[Chem. 52]
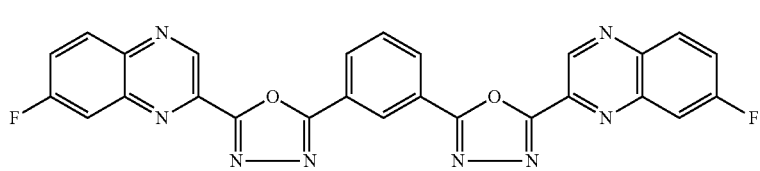
(52)
[Chem. 53]
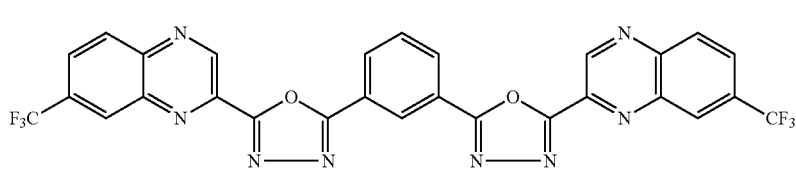
(53)
[Chem. 54]
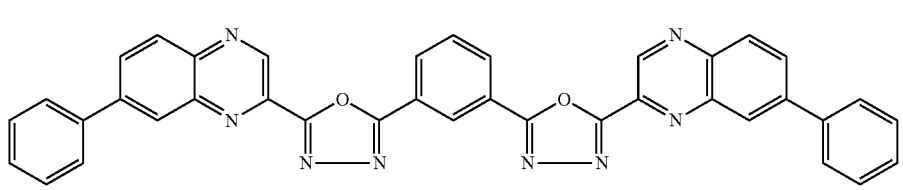
(54)
[Chem. 55]
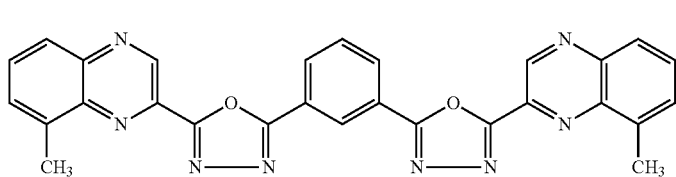
(55)
[Chem. 56]
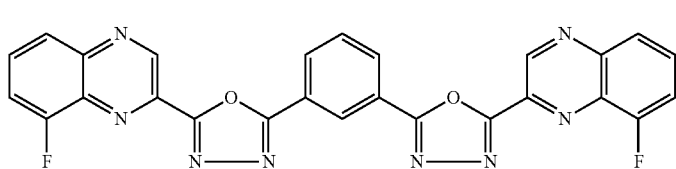
(56)

[Chem. 57]
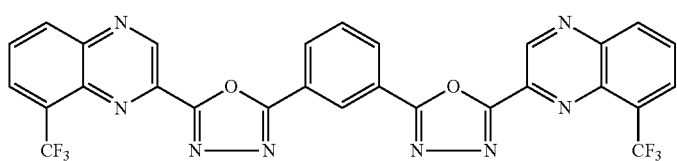
(57)
[Chem. 58]
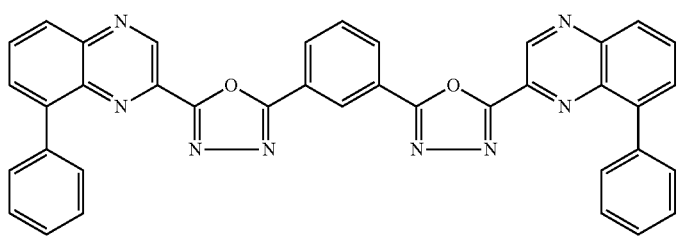
(58)
[Chem. 59]
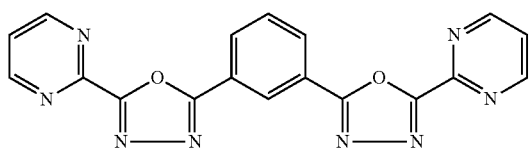
(59)
[Chem. 60]
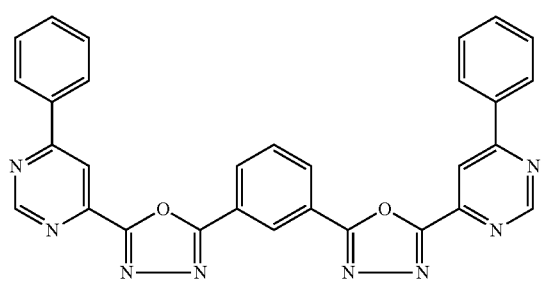
(60)
[Chem. 61]
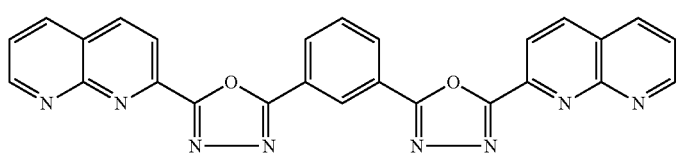
(61)
[Chem. 62]
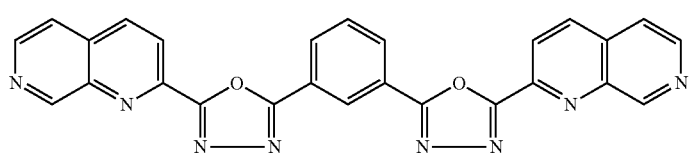
(62)
[Chem. 63]
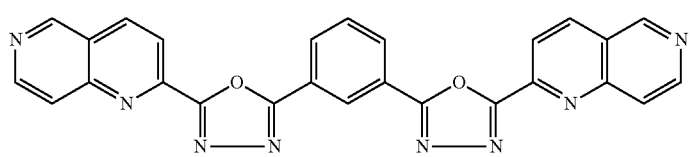
(63)

-continued
[Chem. 64]
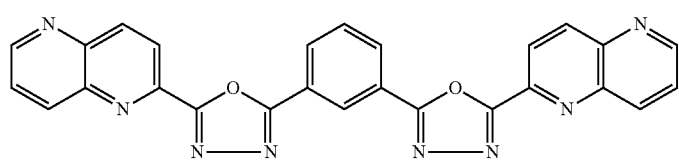
(64)
[Chem. 65]
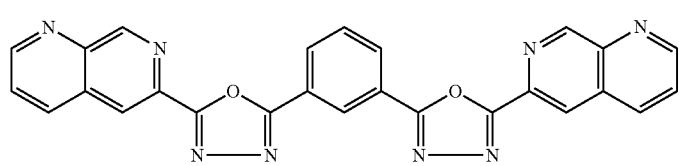
(65)
[Chem. 66]
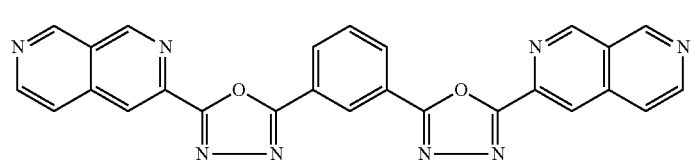
(66)
[Chem. 67]
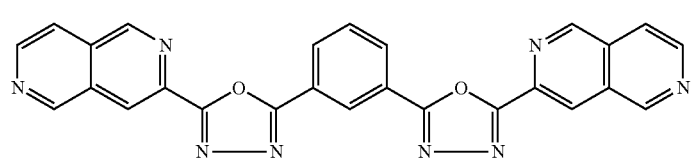
(67)
[Chem. 68]
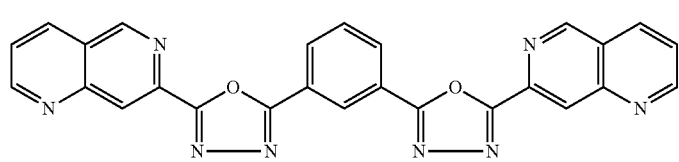
(68)
[Chem. 69]
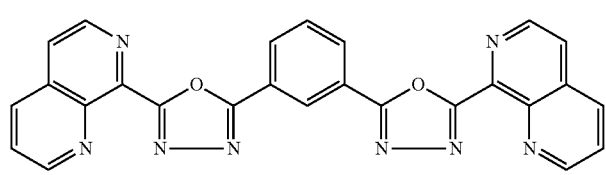
(69)
[Chem. 70]
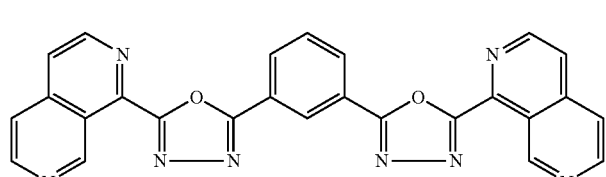
(70)
[Chem. 71]
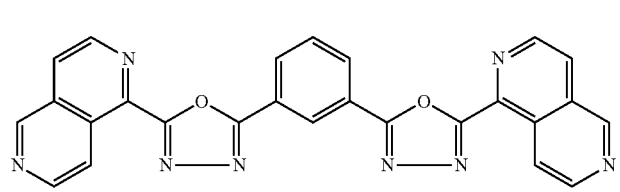
(71)

[Chem. 72]
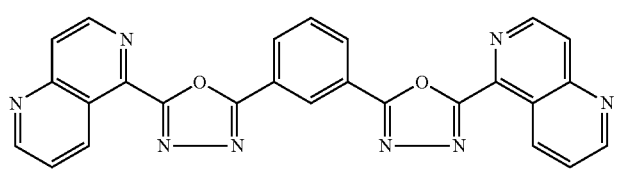
(72)
[Chem. 73]
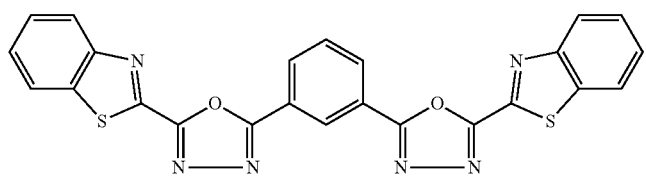
(73)
[Chem. 74]
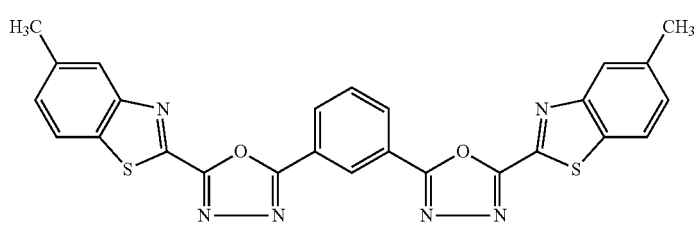
(74)
[Chem. 75]
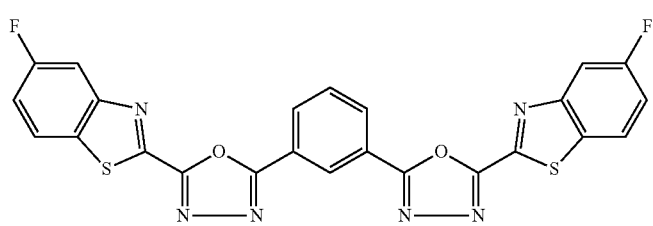
(75)
[Chem. 76]
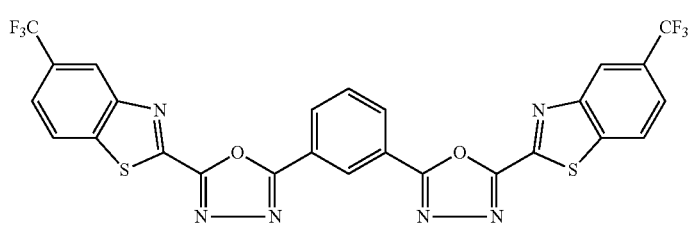
(76)
[Chem. 77]
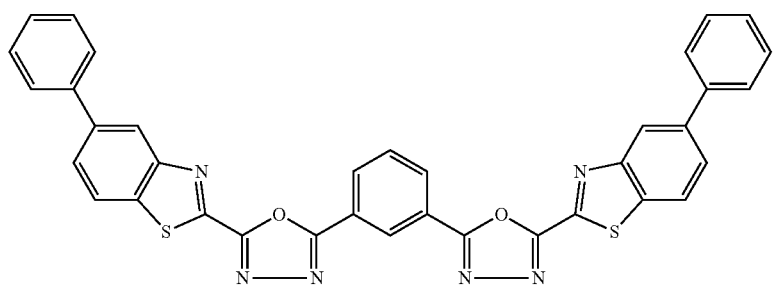
(77)

-continued
[Chem. 78]
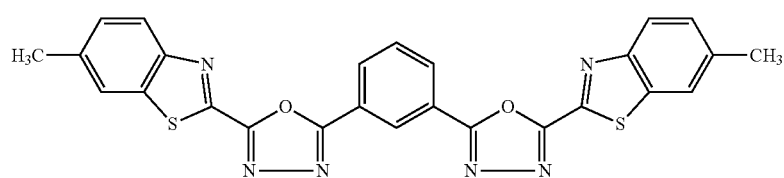
(78)
[Chem. 79]
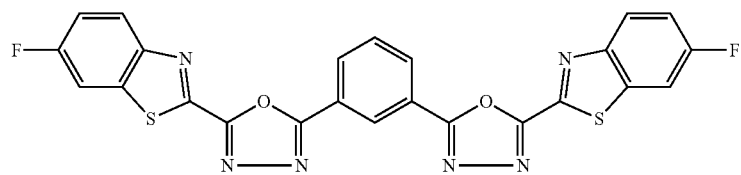
(79)
[Chem. 80]
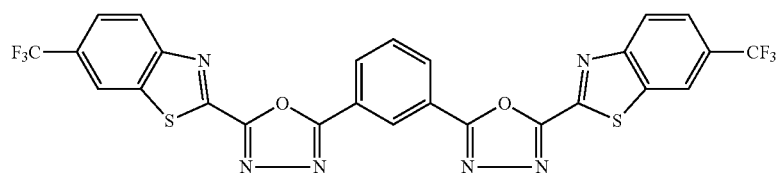
(80)
[Chem. 81]
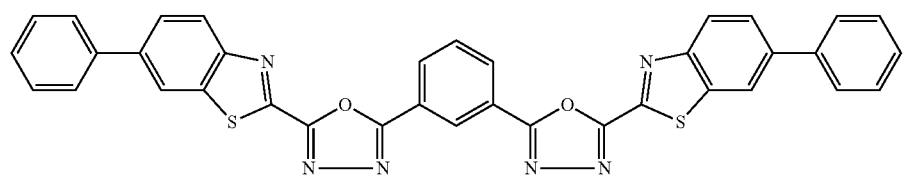
(81)
[Chem. 82]
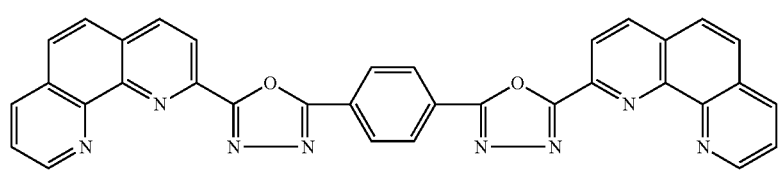
(82)
[Chem. 83]
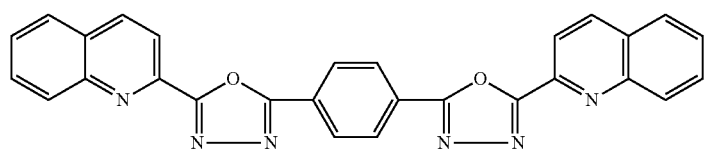
(83)
[Chem. 84]
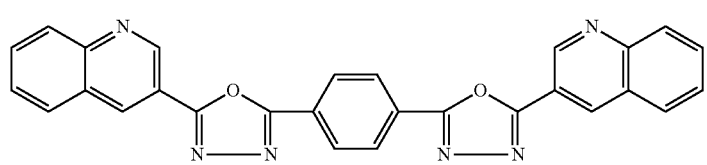
(84)

[Chem. 85]
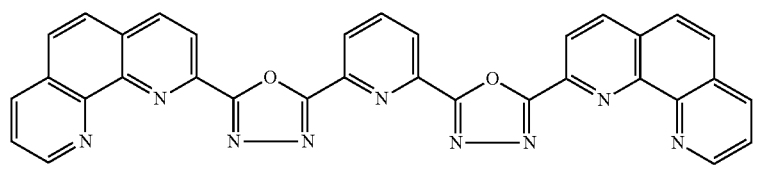
(85)
[Chem. 86]
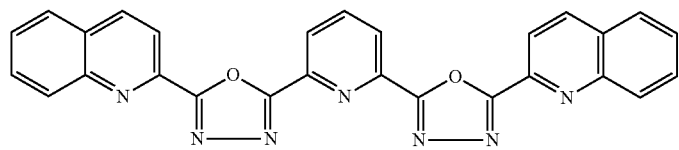
(86)
[Chem. 87]
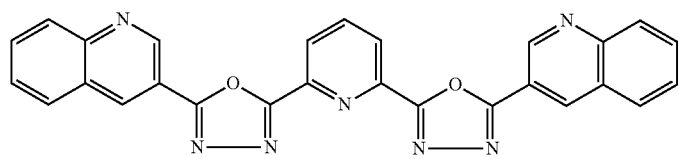
(87)
[Chem. 88]
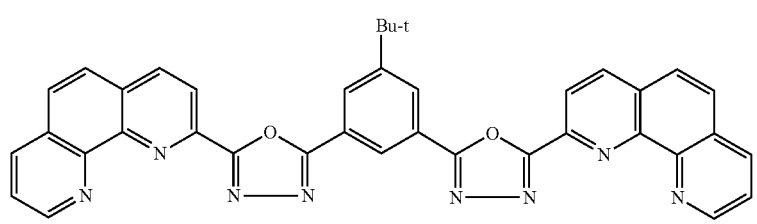
(88)
[Chem. 89]
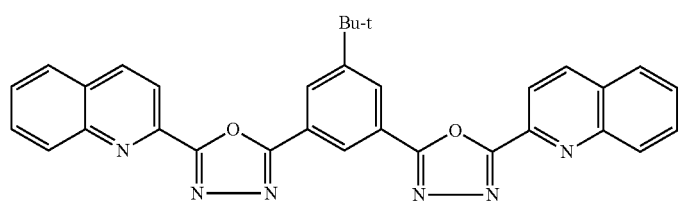
(89)
[Chem. 90]
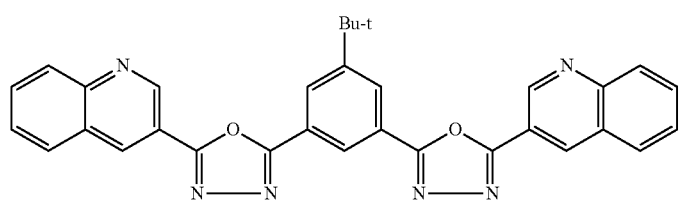
(90)

[Chem. 91]
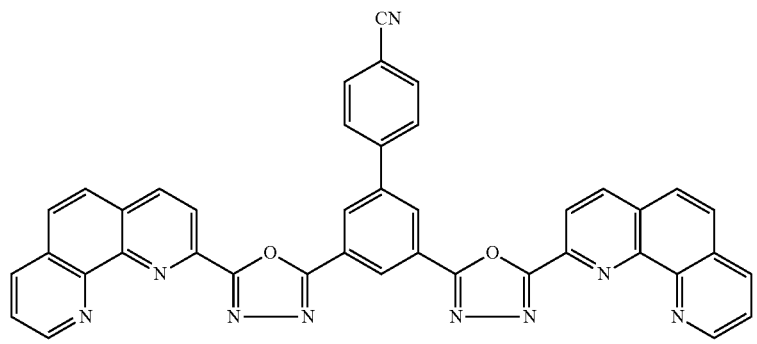
(91)
[Chem. 92]
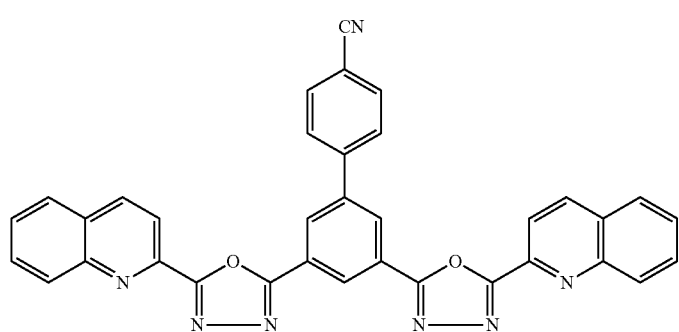
(92)
[Chem. 93]
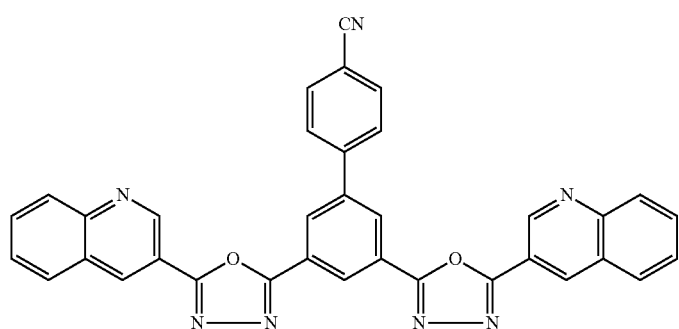
(93)
[Chem. 94]
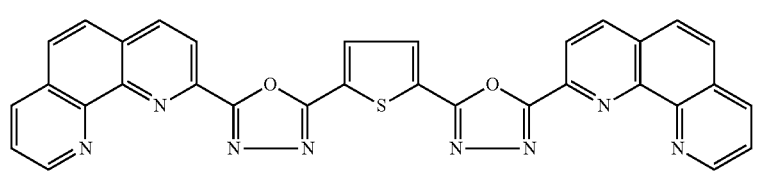
(94)
[Chem. 95]
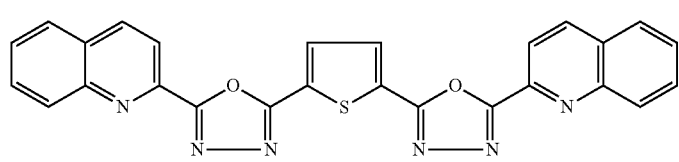
(95)

-continued
[Chem. 96]
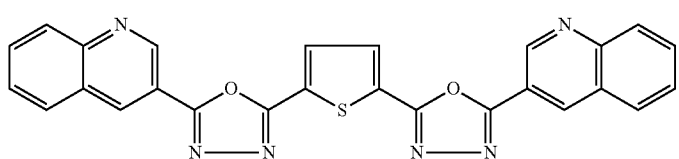
(96)
[Chem. 97]
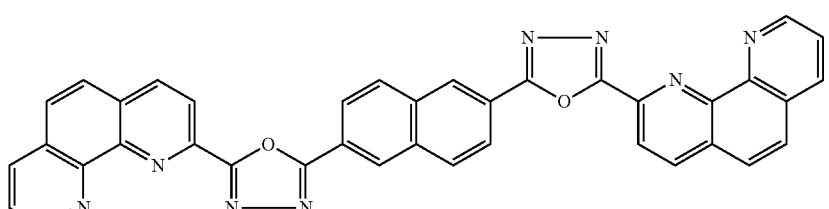
(97)
[Chem. 98]
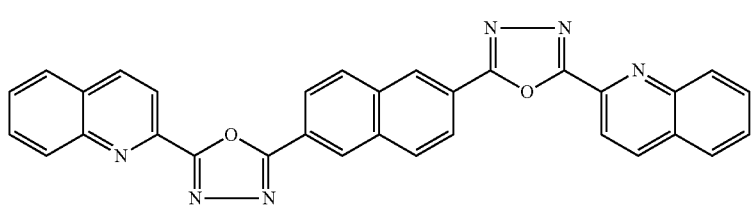
(98)
[Chem. 99]
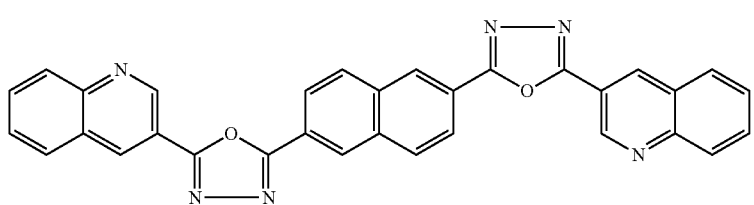
(99)
[Chem. 100]
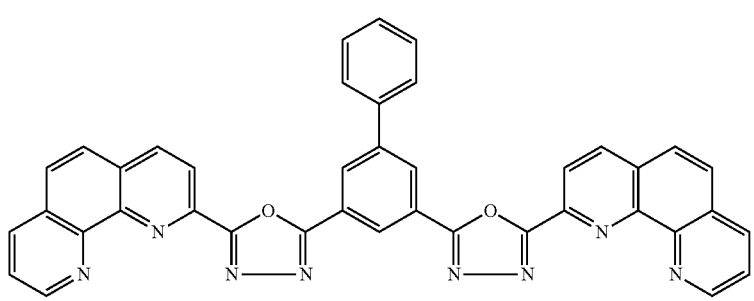
(100)
[Chem. 101]
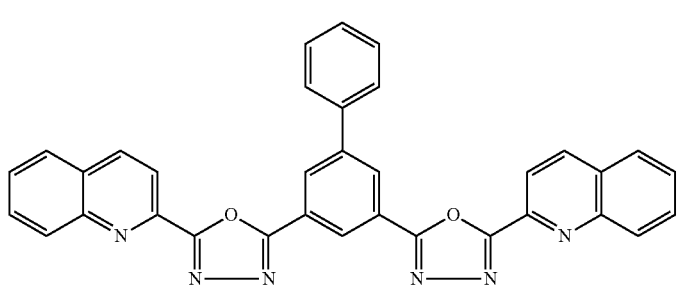
(101)

-continued
[Chem. 102]
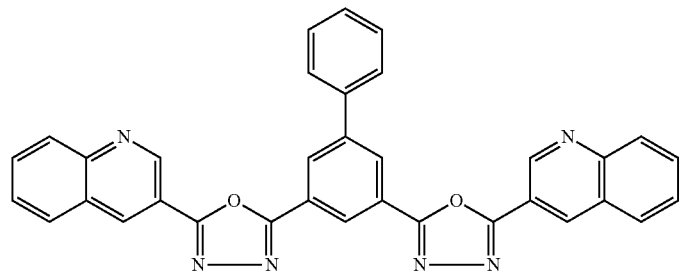
(102)
[Chem. 103]
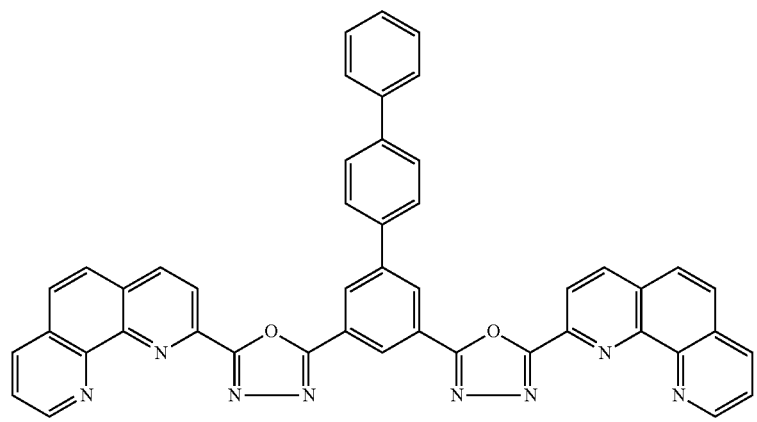
(103)
[Chem. 104]
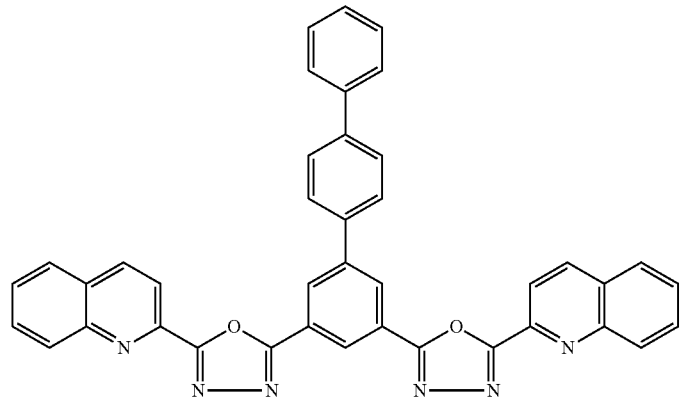
(104)

[Chem. 105]

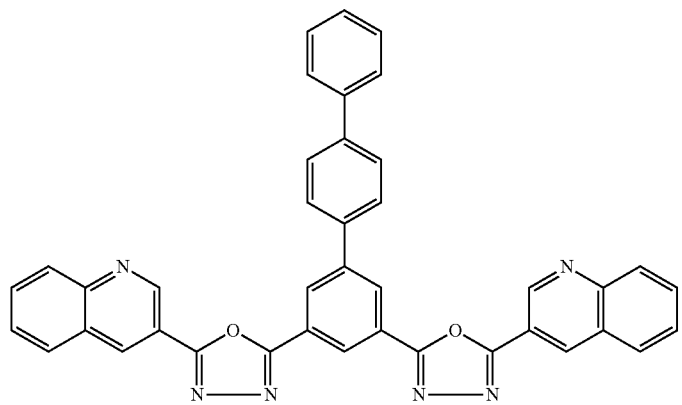

(105)

Purification of these compounds was carried out by column chromatography purification, adsorption purification, recrystallization using a solvent, a crystallization method, or the like. The compounds were identified by NMR analysis.

Examples of the structure of the organic EL device of this invention include a structure wherein an anode, a hole injection layer, a hole transport layer, an emitting layer, a hole blocking layer, an electron transport layer, an electron injection layer, and a cathode are formed in this order on a substrate. In the multi-layer structure, it is possible to omit an organic layer(s) and to use a single material for serving as plural layers in combination.

As the anode of the organic EL device, an electrode material having a large work function such as ITO and gold may be used. As the hole injection layer, a material such as copper phthalocyanine (hereinafter abbreviated as CuPc), a triphenylamine derivative of starburst type, and a tris[p-N-phenyl-α-naphthylamino]phenyl]amine and a coating type material may be used.

As the hole transport layer, various triphenylamine tetramers including benzidine derivatives such as N,N'-diphenyl-N, N'-di(m-tolyl)benzidine and N,N'-diphenyl-N,N'-di(α-naphthyl)benzidine (hereinafter abbreviated as NPD), and N,N'-bis(4-diphenylamino-4'-biphenyl)-N,N'-diphenyl(1,1'-biphenyl)-4,4'-diamine (hereinafter abbreviated as EL022) and the like may be used.

As the emitting layer, the hole blocking layer, and the electron transport layer of the organic EL device, a quinolinium complex, a carbazole derivative, a polydialkylfluorene derivative, and the like may be used as well as the compound having an oxadiazole ring structure bonded with an aromatic heterocycle.

It is possible to produce a high performance organic EL device by using a conventional luminescent material such as a quinolinium complex or a styryl derivative for the emitting layer and using the compound having an oxadiazole ring structure bonded with an aromatic heterocycle as the hole blocking layer, the electron transport layer, or the electron injection layer. Also, it is possible to produce a high performance organic EL device by adding a dopant which is a fluorescent material such as quinacridone, coumarin or rubrene, or a phosphorescent material such as an iridium complex of phenylpyridine as the host material of the emitting layer.

Further, a layer obtained by overlaying or co-depositing a conventional electron transport material on the compound having an oxadiazole ring structure bonded with an aromatic heterocycle may be used as the electron transport layer.

Though it is possible to omit the electron injection layer in the organic EL device of this invention since the compound of this invention having an oxadiazole ring structure bonded with an aromatic heterocycle has a high electron injection function, the organic EL device may have an electron injection layer. As the electron injection layer, lithium fluoride and the like may be used. As the cathode, an electrode material having a low work function such as an alloy of aluminum, magnesium, and silver may be used.

Embodiments of the present invention will be illustrated in greater detail with reference to the following Examples, but the invention should not be construed as being limited thereto so long as not exceeding the gist thereof.

Example 1

Synthesis of 1,3-bis[2-(1,10-phenanthroline-2-yl)-1, 3,4-oxadiazole-5-yl]benzene (hereinafter abbreviated as PhenOXDm) (2)

After dissolving 5.0 g of 2-(2H-tetrazole-5-yl)-1,10-phenanthroline into 50 ml of dehydrated pyridine, 2.1 g of isophthaloylchloride was added. The mixture was heated to 100° C. and stirred under reflux for 5 hours. After cooling to a room temperature, the reaction solution was poured into water to collect a precipitated solid by suction filtration, and the solid was washed with water. The solid was dried under vacuum at 70° C. for 20 hours to obtain a brownish crude product. After dissolving the thus-obtained crude product into a mixed solution of chloroform:methanol=4:1, hexane was added to allow purification by crystallization, thereby obtaining 4.82 g of PhenOXDm (2) (yield: 84%). NMR analysis (see FIG. 1) was performed for identification of the product. The results of the NMR analysis are as follows. 9.15 ppm (2H), 8.89 ppm (1H), 8.73 ppm (2H), 8.59 ppm (2H), 8.50 ppm (2H), 8.45 ppm (2H), 8.07 ppm (4H), 7.97 ppm (1H), 7.78 ppm (2H).

Example 2

The melting point and the glass transition point of the compound (2) of Example 1 were measured by a high sensitivity differential scanning calorimeter (DSC3100S; product of Bruker AXS K.K.). The melting point was 199° C., and the glass transition point was 178° C.

The compound (2) of Example 1 has a high glass transition point and is stable in its thin film state.

Example 3

A vapor deposition film having a film thickness of 100 nm was formed on an ITO substrate by using the compound (2) of Example 1, and a work function thereof was measured by an atmospheric photoelectron spectrometer (AC3; product of Riken Keiki Co., Ltd.). The work function was 6.09 eV.

Example 4

Synthesis of 1,3-bis[2-(quinoline-2-yl)-1,3,4-oxadia-zole-5-yl]benzene (hereinafter abbreviated as 2QOXDm) (14)

Figure 2:
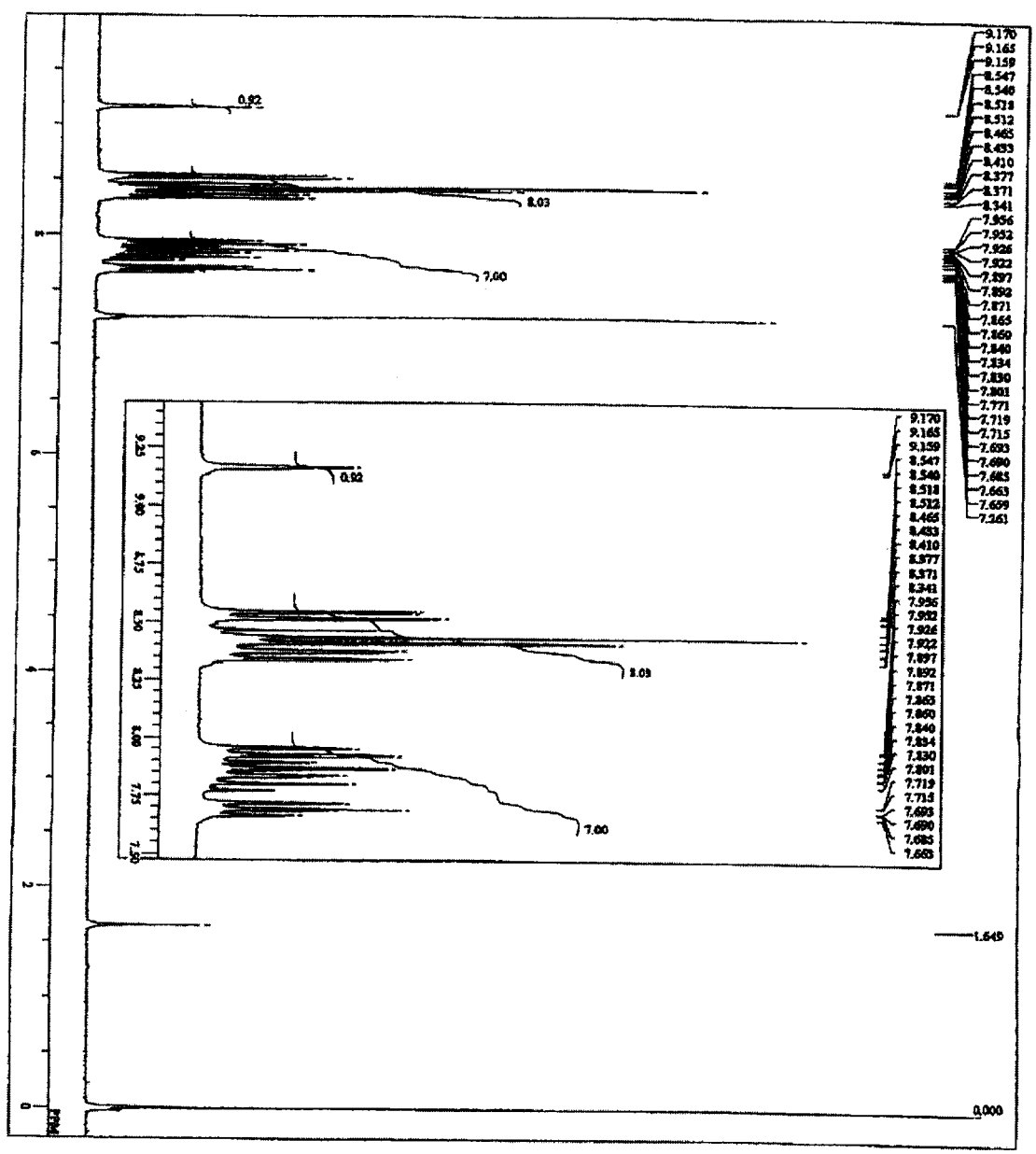
FIG. 2 is a 1H-NMR chart of 2QOXDm.
Figure 3:
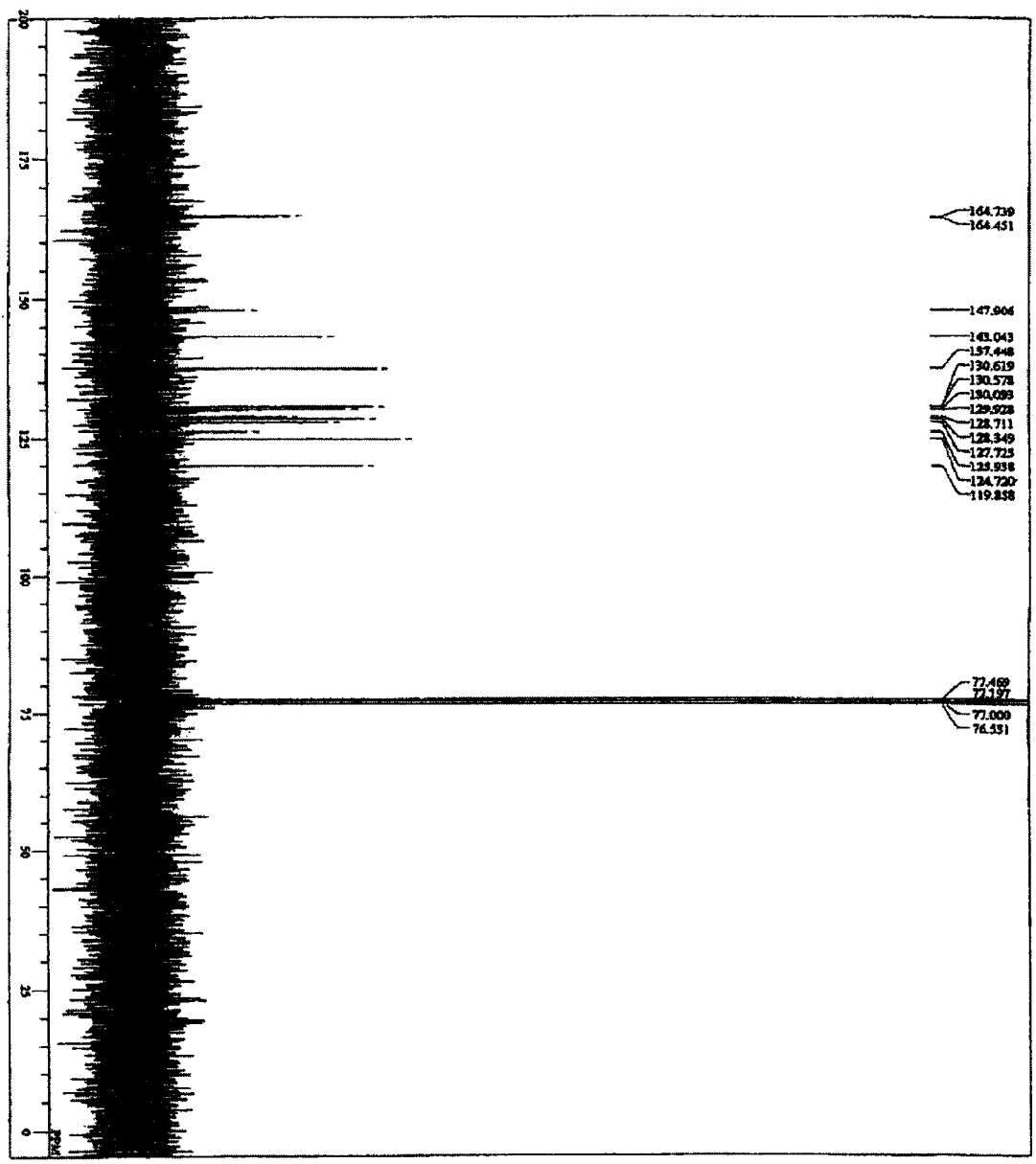
FIG. 3 is a 13C-NMR chart of 2QOXDm.

After dissolving 4.0 g of 2-(2H-tetrazole-5-yl)quinoline into 60 ml of dehydrated pyridine, 2.1 g of isophthaloylchloride was added. The mixture was heated to 100° C. and stirred under reflux for 4 hours. After cooling to a room temperature, the reaction solution was poured into water to collect a precipitated solid by suction filtration, and the solid was washed with water. The solid was dried under vacuum at 70° C. for 20 hours to obtain a brownish crude product. After dissolving the thus-obtained crude product into chloroform, hexane was added to allow purification by crystallization, thereby obtaining 4.12 g of 2QOXDm (14) (yield: 87%). NMR analysis (see FIG. 2) was performed for identification of the product. The results of the NMR analysis are as follows. 9.17 ppm (1H), 8.53 ppm (2H), 8.34-8.47 ppm (6H), 7.83-7.96 ppm (4H), 7.80 ppm (1H), 7.69 ppm (2H). Further, signals of all carbon atoms were confirmed (see FIG. 3). 164.7 ppm, 164.5 ppm, 147.9 ppm, 143.0 ppm, 137.4 ppm, ppm, 130.6 ppm, 130.1 ppm, 129.9 ppm, 128.7 ppm, ppm, 127.7 ppm, 125.9 ppm, 124.7 ppm, 119.9 ppm.

Example 5

Synthesis of 1,3-bis[2-(quinoline-3-yl)-1,3,4-oxadia-zole-5-yl]benzene (hereinafter abbreviated as 3QOXDm) (31)

Figure 4:
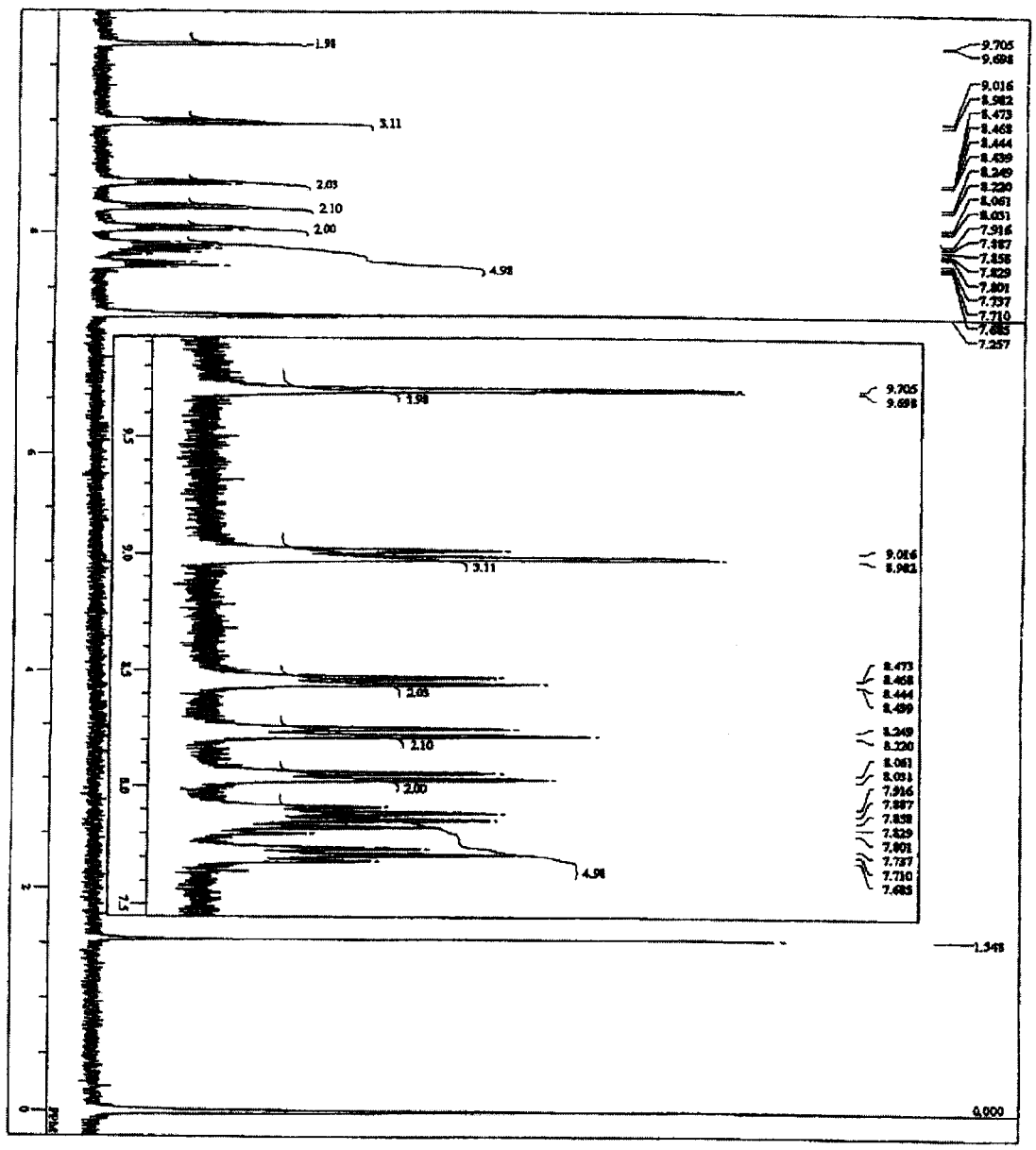
FIG. 4 is a 1H-NMR chart of 3QOXDm.

After dissolving 4.0 g of 3-(2H-tetrazole-5-yl)-quinoline into 60 ml of dehydrated pyridine, 2.1 g of isophthaloylchloride was added. The mixture was heated to 100° C. and stirred under reflux for 3 hours. After cooling to a room temperature, the reaction solution was poured into water to collect a precipitated solid by suction filtration, and the solid was washed with water. The solid was dried under vacuum at 70° C. for 20 hours to obtain a grayish white crude product. After dissolving the thus-obtained crude product into chloroform, hexane was added to allow purification by crystallization, thereby obtaining 3.90 g of 3QOXDm (31) (yield: 82%). NMR analysis (see FIG. 4) was performed for identification of the product. The results of the NMR analysis are as follows. 9.70 ppm (2H), 9.02 ppm (1H), 8.98 ppm (2H), 8.46 ppm (2H), 8.24 ppm (2H), 8.05 ppm (2H), 7.89 ppm (2H), 7.83 ppm (1H), 7.71 ppm (2H).

Example 6

Figure 5:
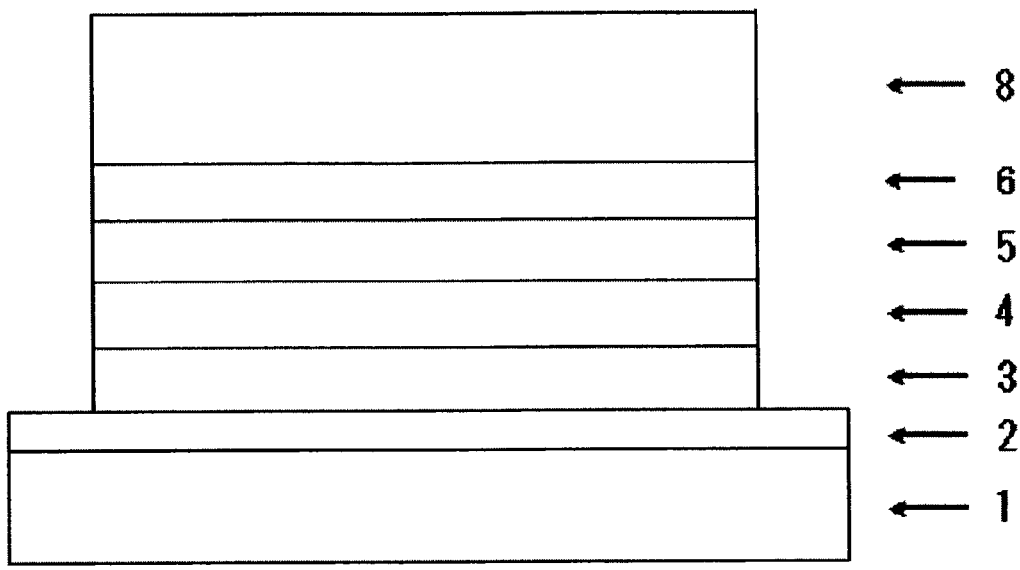
FIG. 5 is a diagram showing the structure of EL device of Example 6.

An organic EL device was obtained by vapor-depositing, on a glass substrate 1 on which an ITO electrode had been formed as a transparent anode 2, a hole injection 3, a hole transport layer 4, an emitting layer 5, a hole blocking layer-cum-electron transport layer 6, and a cathode (aluminum electrode) 8 in this order as shown in FIG. 5. The glass substrate 1 on which an ITO film having a film thickness of 150 nm had been formed was washed with an organic solvent and then subjected to washing of its surface by an oxygen plasma treatment. The glass substrate was placed in a vacuum vapor deposition machine, followed by pressure reduction to below 0.001 Pa.

Subsequently, about 20 nm of CuPc was formed as the hole injection layer 3 at a vapor deposition rate of 6 nm/min. Thereon, about 40 nm of NPD was formed as the hole transport layer 4 at a vapor deposition rate of 6 nm/min. On the hole transport layer 4, about 30 nm of Alq was formed as the emitting layer 5 at a vapor deposition rate of 6 nm/min. On the emitting layer 5, about 30 nm of PhenOXDm (2) which is the compound of Example 1 was formed as the hole blocking layer-cum-electron transport layer 6 at a vapor deposition rate of 2 nm/min. The foregoing vapor depositions were each conducted without breaking the vacuum. After boat replacement and pressure reduction, about 200 nm of an alloy of magnesium and silver was formed as the cathode 8 by simultaneously vapor-depositing magnesium and silver at a ratio of 10:1 on the hole blocking layer-cum-electron transport layer 6. The thus-obtained device was stored in a vacuum desiccator, and characteristic measurements were performed in the air at an ordinary temperature.

The thus-obtained organic EL device generated stable green luminescence and exhibited luminescence of 1,070 cd/m$^2$ at a driving voltage of 7.0 V and luminescence of 3,600 cd/m$^2$ at a driving voltage of 8.0 V.

A ratio obtained by dividing the number of photons emitted from the organic EL device by the number of electrons injected into the organic EL device is called an external quantum efficiency. The external quantum efficiencies of this device at 10,000 cd/m$^2$, 15,000 cd/m$^2$, and 20,000 cd/m$^2$ were 1.05%, 1.03%, and 0.99%, respectively.

A maximum luminance before breakpoint was evaluated by increasing the load of the current density by increasing the driving voltage. Since the maximum luminance measured by the method reflects electrical stability of the device, the maximum luminance serves as an index of the durability of the organic EL device.

The device exhibited the maximum luminance of 27,000 cd/m$^2$ at 9.6 V, and then the luminance of luminescence was diminished to reach the breakpoint.

Comparative Example 1

For comparison, an organic EL device was produced under the same conditions as in Example 6 except for using Alq as the material for a hole blocking layer-cum-electron transport layer 6, and the characteristics thereof were examined. Specifically, about 60 nm of Alq was formed as the hole blocking layer-cum-electron transport layer 5 and 6 at a vapor deposition rate of 6 nm/min. The thus-obtained organic EL device exhibited luminescence of 490 cd/m$^2$ at a driving voltage of 7.0 V and luminescence of 1,680 cd/m$^2$ at a driving voltage of 8.0 V. External quantum efficiencies of the device at 10,000 cd/m$^2$ and 15,000 cd/m$^2$ were 0.92% and 0.59%, respectively. The device exhibited the maximum luminance of 15,200 cd/m$^2$ at V, and then the luminance of luminescence was diminished to reach the breakpoint.

As is apparent from the above results, the organic EL device obtained by using PhenOXDm (2) which is the compound of Example 1 having an oxadiazole ring structure bonded with an aromatic heterocycle has a stable luminescent efficiency as compared to the device obtained by using Alq which is an ordinary used electron transport material. Also, the luminance of luminescence of the device was about twice at the identical voltage, and that the maximum luminance before breakpoint of the device was also about twice.

From the foregoing results, it is apparent that the organic EL device of this invention achieves good device efficiency, high electrical stability, and good durability as compared to the device using Alq.

Example 7

An organic EL device was produced under the same conditions as in Example 6 except for using 2QOXDm (14) which is the compound of Example 4 as the material for the hole blocking layer-cum-electron transport layer 6, and the characteristics thereof were examined. About 30 nm of 2QOXDm (14) was formed as the hole blocking layer-cum-electron transport layer 6 at a vapor deposition rate of 3 nm/min. The thus-obtained organic EL device exhibited green luminescence of 700 cd/m² at 7.0 V and green luminescence of 2,140 cd/m² at 8.0 V.

Example 8

Figure 6:
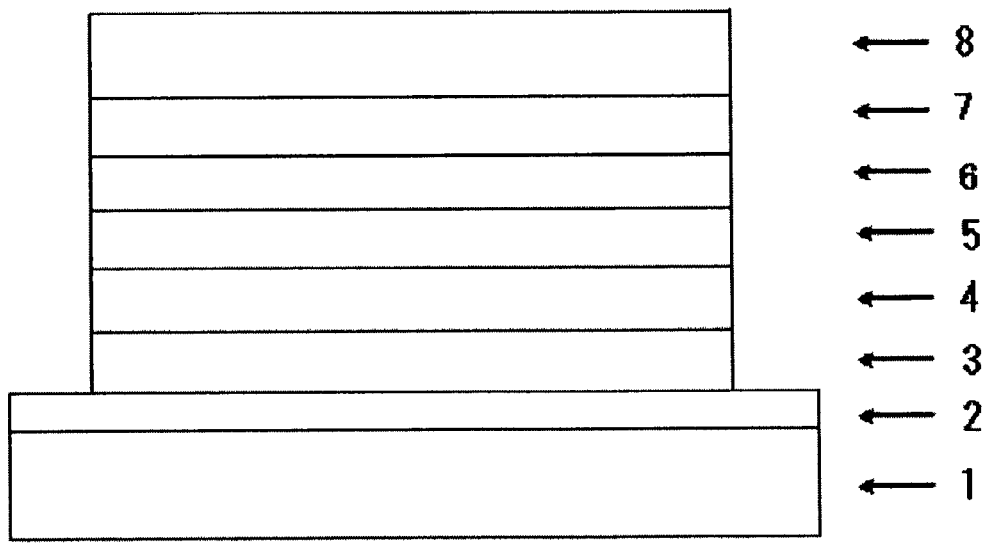
FIG. 6 is a diagram showing a structure of EL device of Example 8.

An organic EL device was obtained by vapor-depositing, on a glass substrate 1 on which an ITO electrode had been formed as a transparent anode 2, a hole injection layer 3, a hole transport layer 4, an emitting layer 5, a hole blocking layer-cum-electron transport layer 6, an electron injection layer 7, and a cathode 8 in this order as shown in FIG. 6. The glass substrate 1 on which an ITO film having a film thickness of 150 nm had been formed was washed with an organic solvent and then subjected to washing of its surface by an oxygen plasma treatment. The glass substrate was placed in a vacuum vapor deposition machine, followed by pressure reduction to below 0.001 Pa.

Subsequently, about 20 nm of CuPc was formed as the hole injection layer 3 at a vapor deposition rate of 6 nm/min. On the hole injection layer 3, about 40 nm of NPD was formed as the hole transport layer 4 at a vapor deposition rate of 6 nm/min. On the hole transport layer 4, about 30 nm of Alq was formed as the emitting layer 5 at a vapor deposition rate of 6 nm/min. On the emitting layer 5, about 30 nm of PhenOXDm (2) which is the compound of Example 1 was formed as the hole blocking layer-cum-electron transport layer 6 at a vapor deposition rate of 2 nm/min. The foregoing vapor depositions were each conducted without breaking the vacuum. After boat replacement and pressure reduction, about 0.5 nm of lithium fluoride was formed as the electron injection layer 7 on the hole blocking layer-cum-electron transport layer 6 at a vapor deposition rate of 0.6 nm/min. About 200 nm of aluminum was vapor-deposited on the electron transport layer 7 to form the cathode 8. The thus-obtained device was stored in a vacuum desiccator, and characteristic measurement was performed in the air at an ordinary temperature.

The thus-obtained organic EL device exhibited luminescence of 710 cd/m² at a driving voltage of 7.0 V and green luminescence of 2,520 cd/m² at a driving voltage of 8.0 V.

As in the foregoing evaluation results, it was confirmed that the organic EL device of this invention is excellent as compared to the device using Alq which is used as an ordinary electron transport material.

While the present invention has been described and in detail with reference to specific embodiments thereof, it will be apparent to one skilled in the art that various changes and modifications can be made therein without departing from the spirit and scope thereof.

This invention is based on Japanese Patent Application No. 2005-263687 filed on Sep. 12, 2005, and the contents thereof are herein incorporated by reference.

INDUSTRIAL APPLICABILITY

The compound of this invention having an oxadiazole ring structure bonded with an aromatic heterocycle is excellent as a compound for organic EL devices since it enables easy electron transfer and is stable in its thin film state. By producing an organic EL device using the compound, it is possible to increase luminance of luminescence comparing at the same driving voltage and to improve durability.

The invention claimed is:

1. A compound, comprising at least one moiety comprising an oxadiazole ring structure bonded with an aromatic heterocycle, the compound represented by formula (1):

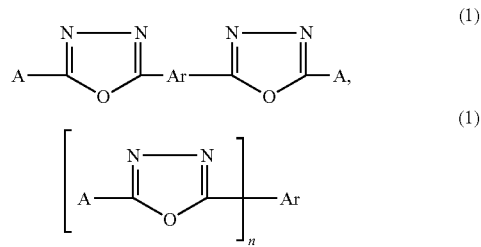

Wherein Ar represents a substituted or unsubstituted aromatic hydrocarbon group, excluding a terphenyl group, a substituted or unsubstituted aromatic heterocyclic group, or a substituted or unsubstituted condensed polycyclic aromatic group; and A represents a substituted or unsubstituted aromatic phenanthryl group, pyronyl group, furanyl group, pyrazolyl group, oxazolyl group, thiazolyl group, pyrimidyl group, triazyl group, thiophenyl group, quinolyl group, quinoxalyl group, benzothiophenyl group, benzooxazolyl group, benzothiazolyl group, benzoimidazolyl group, dibenzofuranyl group, dibenzothiophenyl group, carbazolyl group, an indolyl group or indenyl group.

2. An organic electroluminescence device comprising: a pair of electrodes; and at least one organic layer sandwiched between the pair of electrodes, comprising, in the at least one organic layer, a compound, comprising at least one moiety comprising an oxadiazole ring structure bonded with an aromatic heterocycle, the compound represented by formula (1):

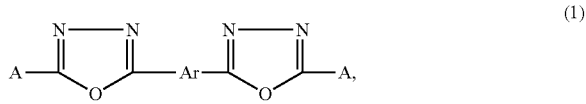

Wherein Ar represents a substituted or unsubstituted aromatic hydrocarbon group, excluding a terphenyl group, a substituted or unsubstituted aromatic heterocyclic group, or a substituted or unsubstituted condensed polycyclic aromatic group; and A represents a substituted or unsubstituted aromatic phenanthryl group, pyronyl group, furanyl group, pyrazolyl group, oxazolyl group, thiazolyl group, pyrimidyl group, triazyl group, thiophenyl group, quinolyl group, quinoxalyl group, benzothiophenyl group, benzooxazolyl group, benzothiazolyl group, benzoimidazolyl group, dibenzofuranyl group, dibenzothiophenyl group, carbazolyl group, an indolyl group or indenyl group.

3. The organic electroluminescence device according to claim 2, wherein the organic layer comprising the compound represented by formula (1) is an electron transport layer.

4. The organic electroluminescence device according to claim 2, wherein the organic layer comprising the compound represented by formula (1) is a hole blocking layer.

5. The organic electroluminescence device according to claim 2, wherein the organic layer comprising the compound represented by formula (1) is an emitting layer.

6. The compound of claim 1, wherein Ar represents a substituted or unsubstituted single ring or fused multi-ring aromatic or heteroaromatic group.

7. The organic electroluminescence device according to claim 2, wherein Ar of the compound represents a substituted or unsubstituted single ring or fused multi-ring aromatic or heteroaromatic group.

8. The organic electroluminescence device according to claim 7, wherein the organic layer comprising the compound represented by formula (1) is an electron transport layer.

9. The organic electroluminescence device according to claim 7, wherein the organic layer comprising the compound represented by formula (1) is a hole blocking layer.

10. The organic electroluminescence device according to claim 7, wherein the organic layer comprising the compound represented by formula (1) is an emitting layer.

11. A compound, selected from the group consisting of

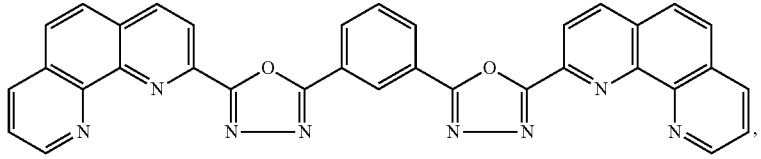

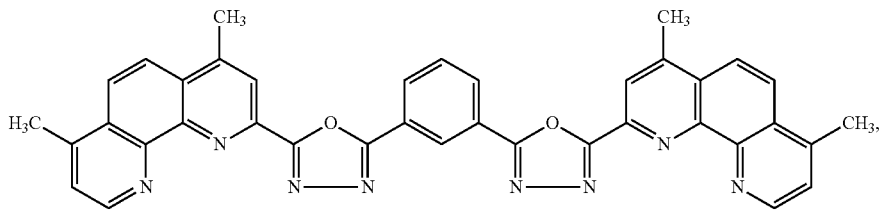

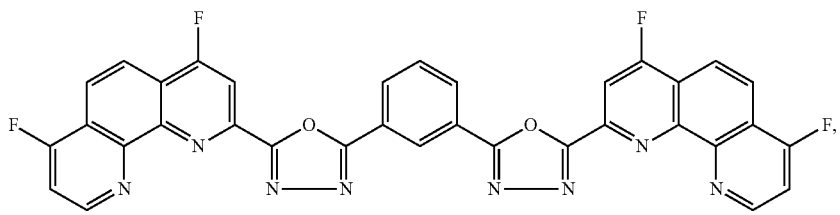

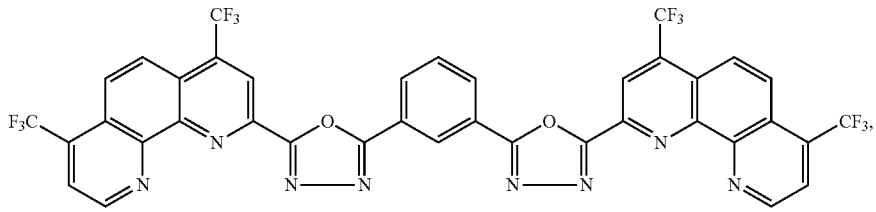

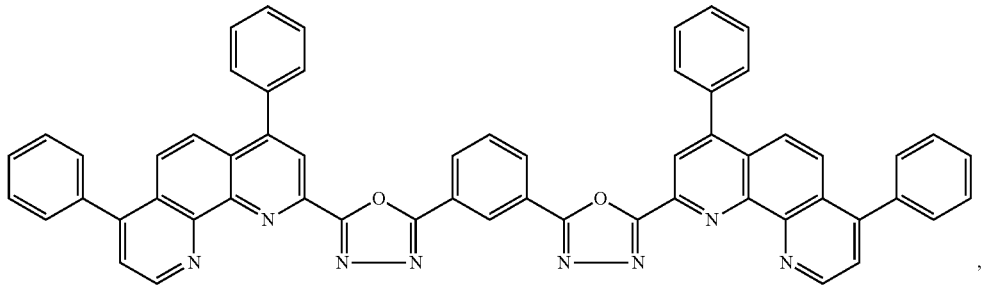

-continued
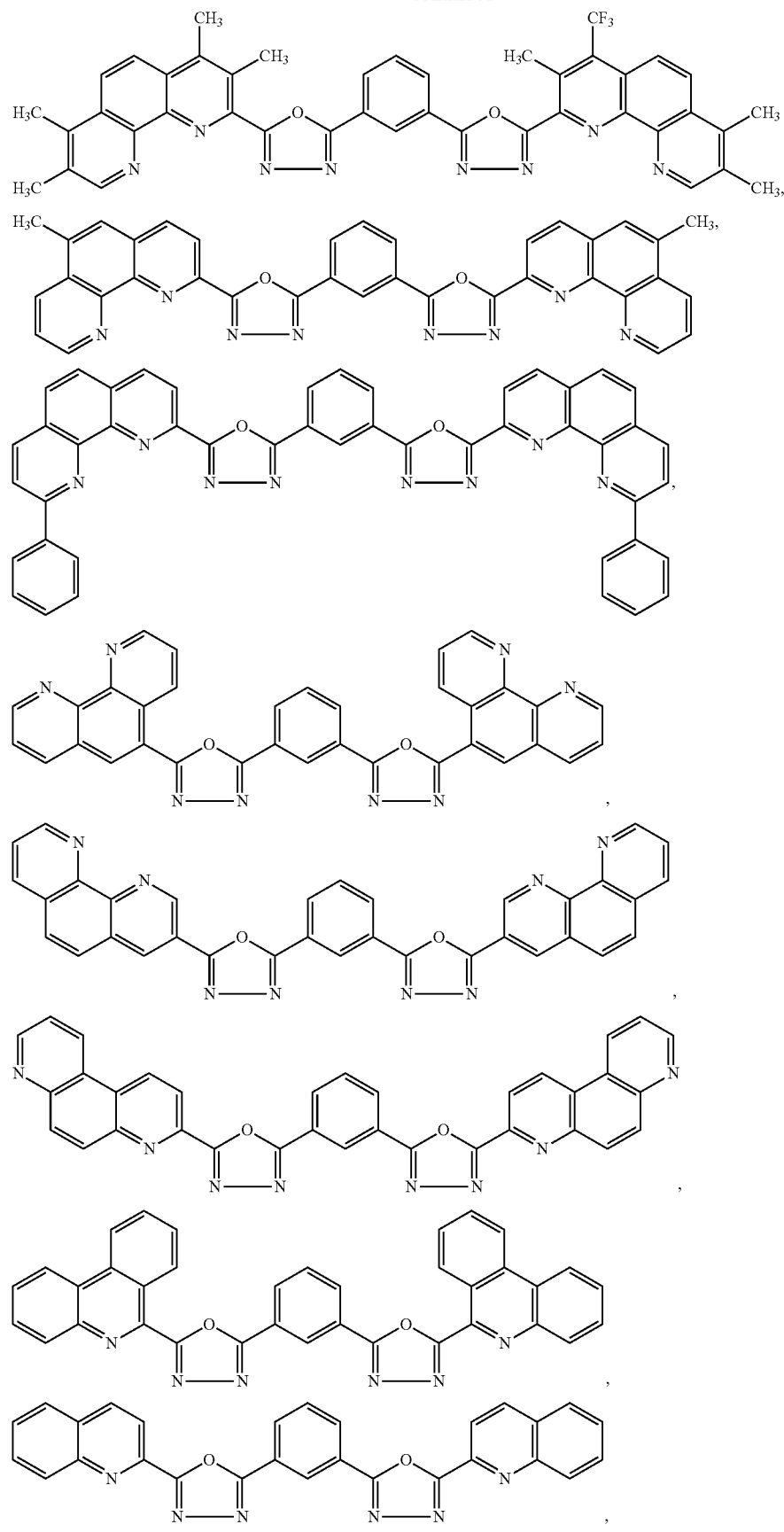

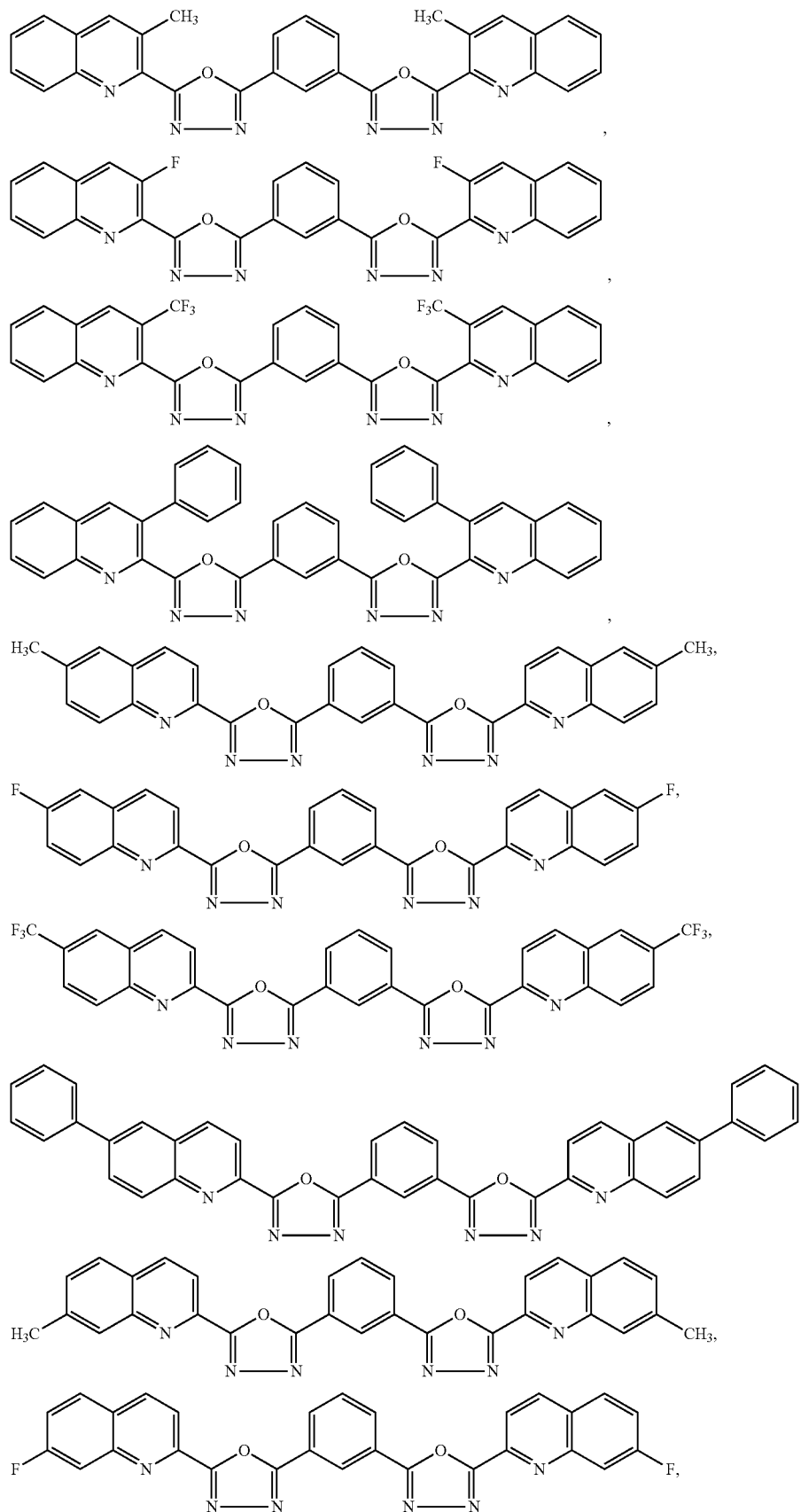

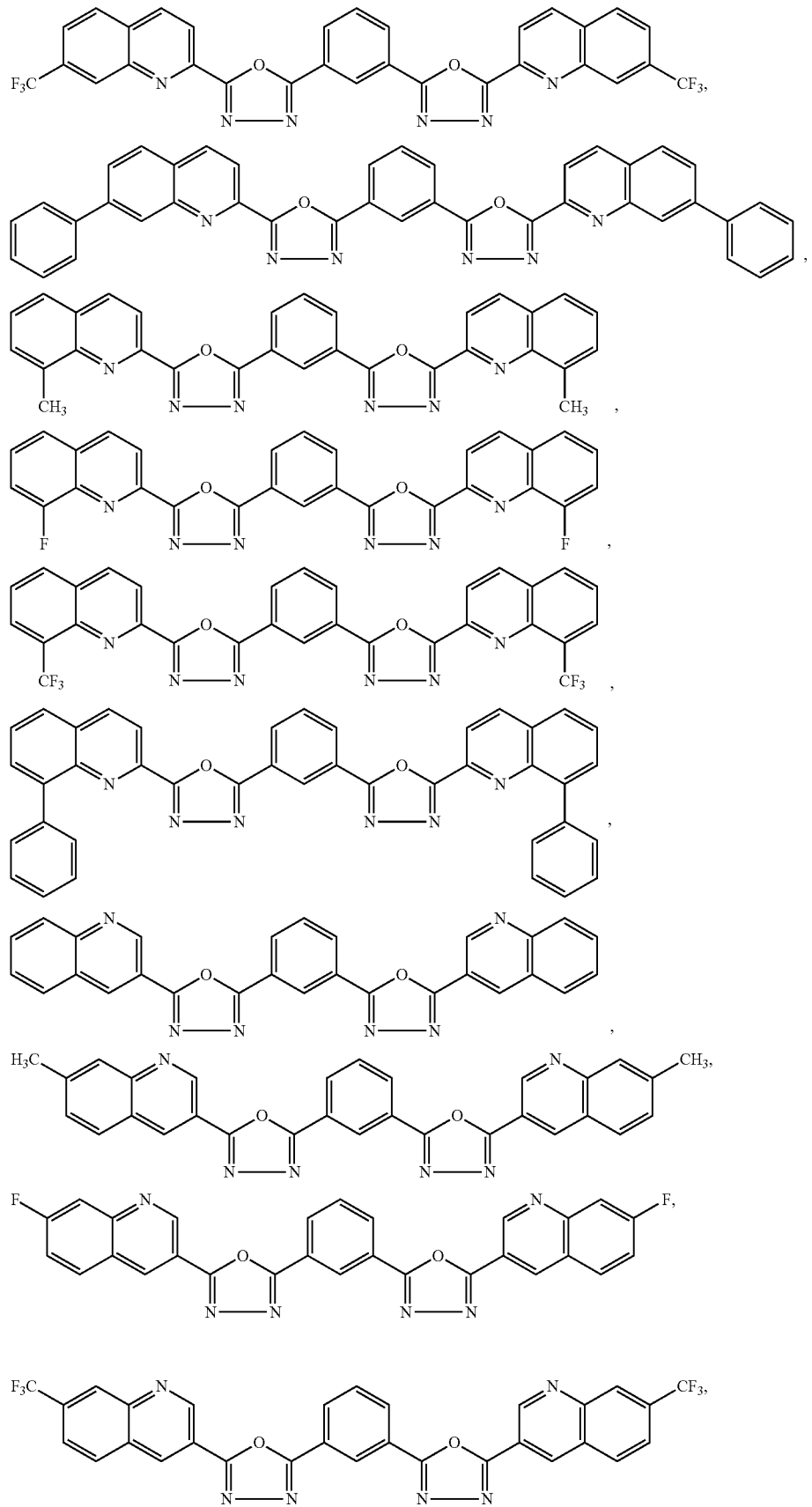

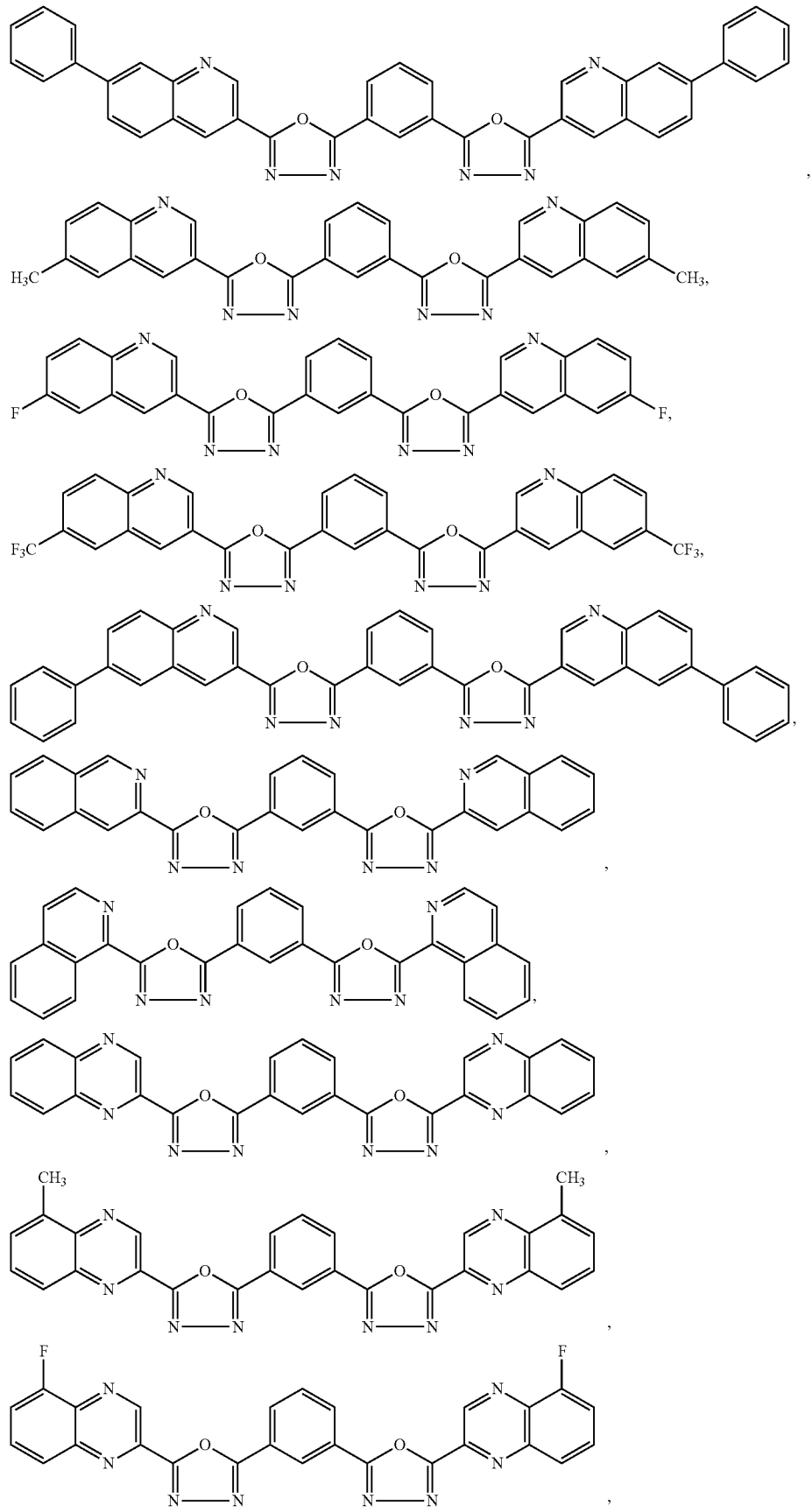

-continued
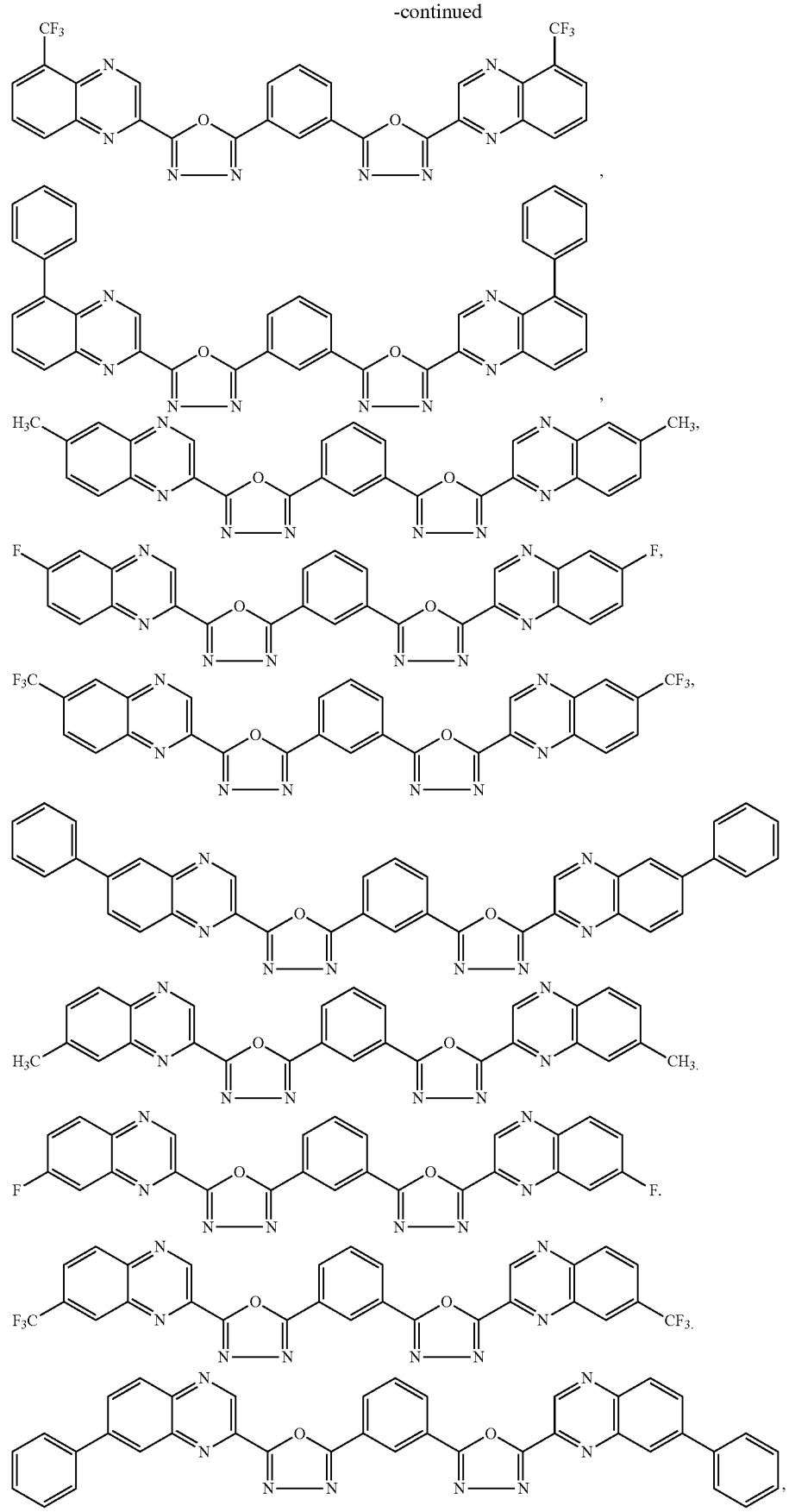

-continued
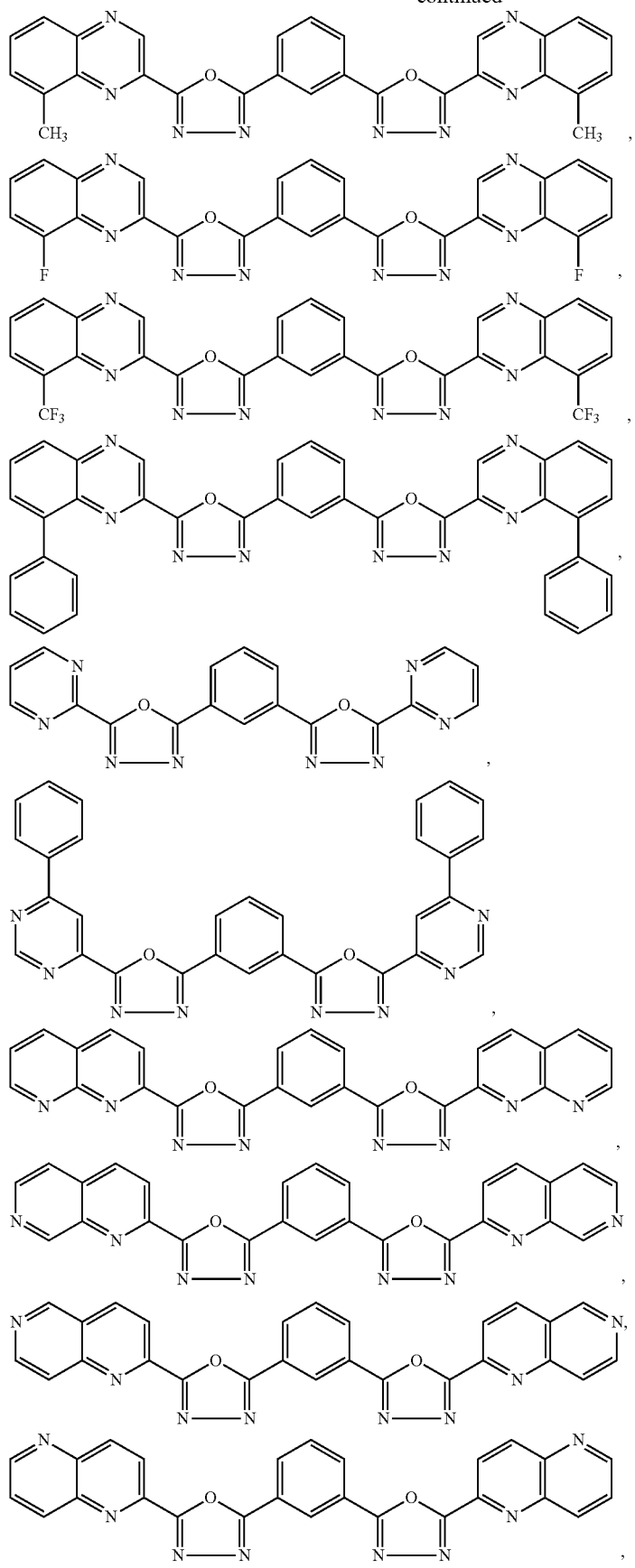

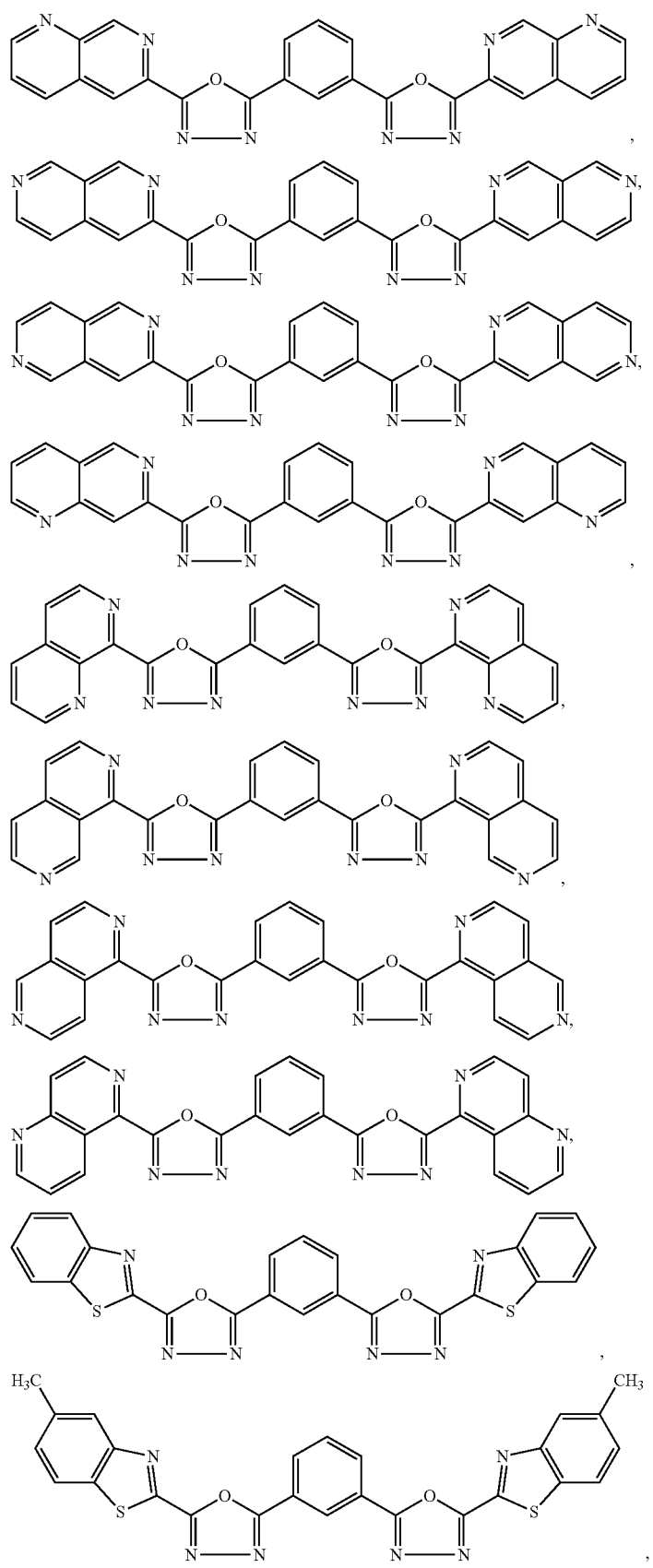

-continued
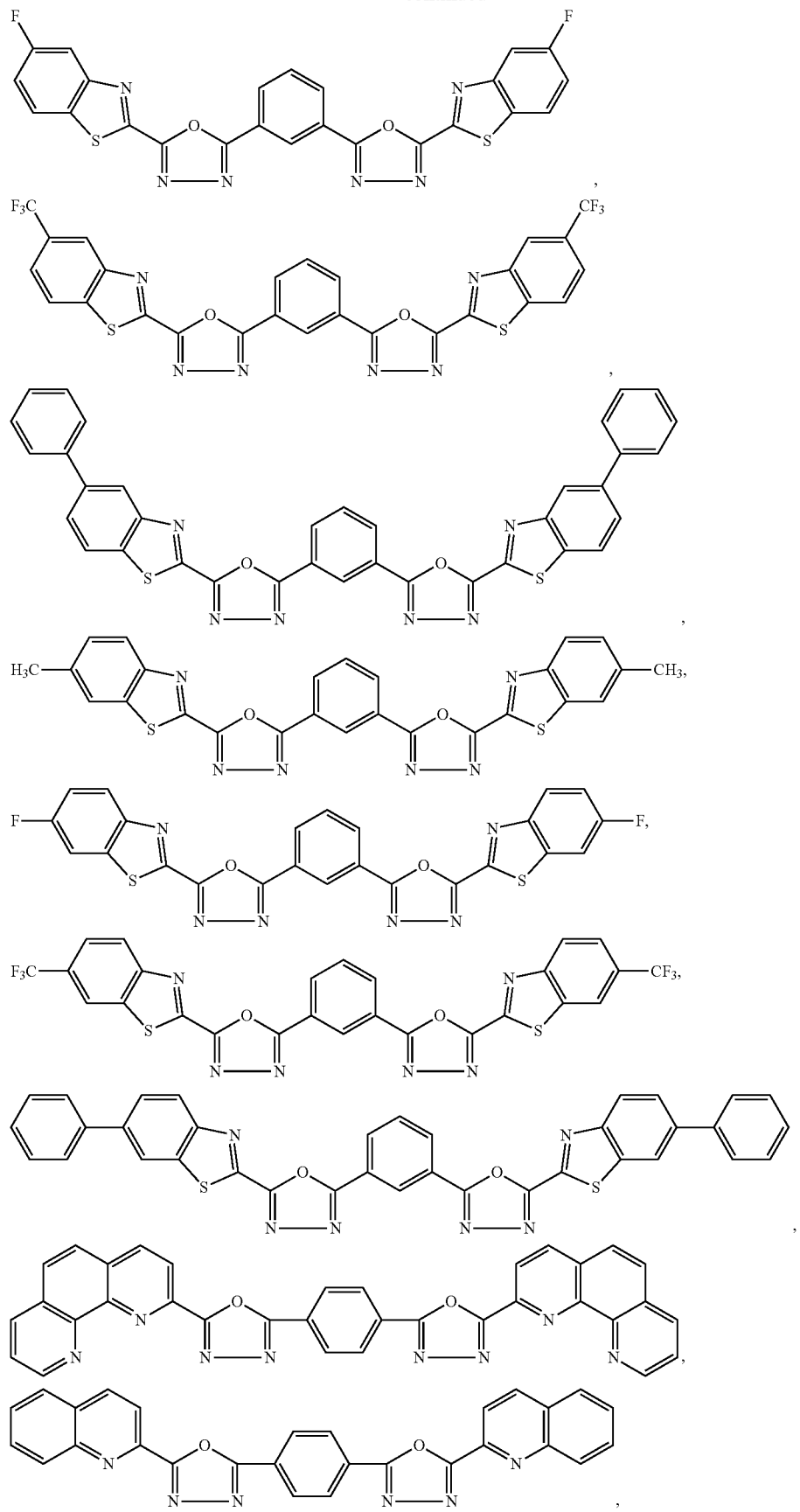

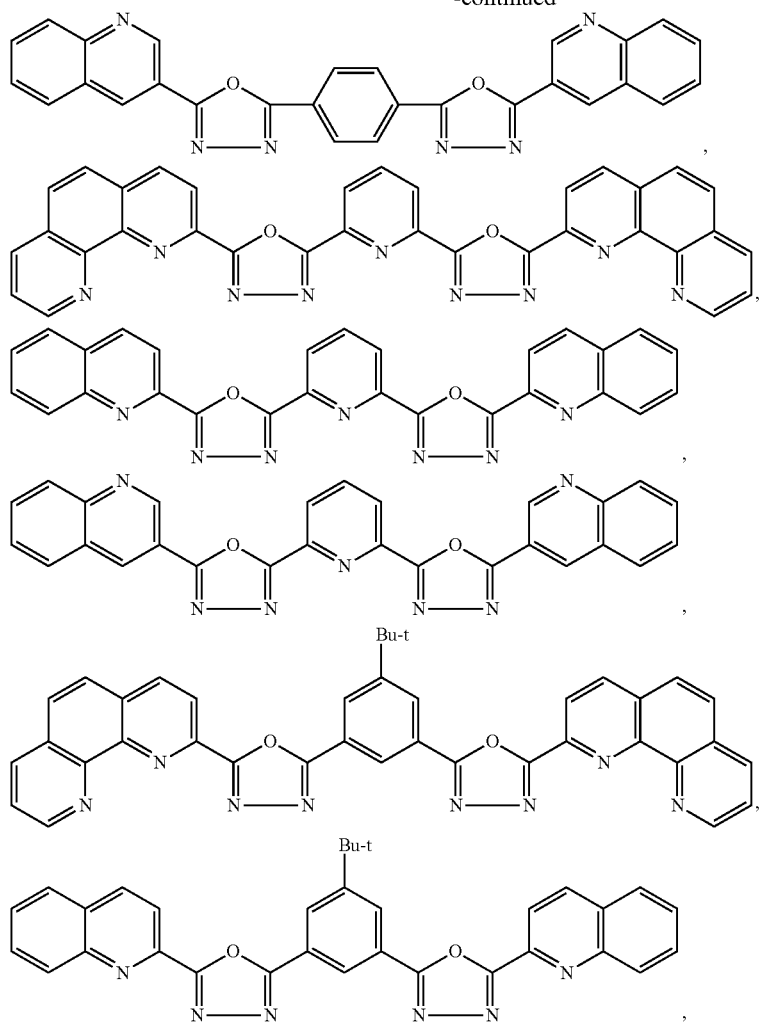
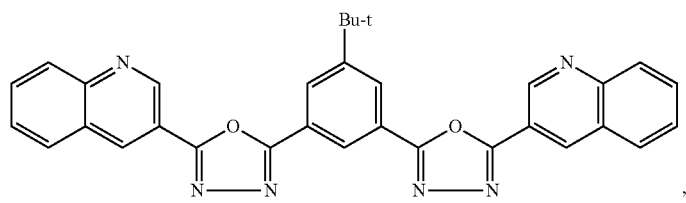
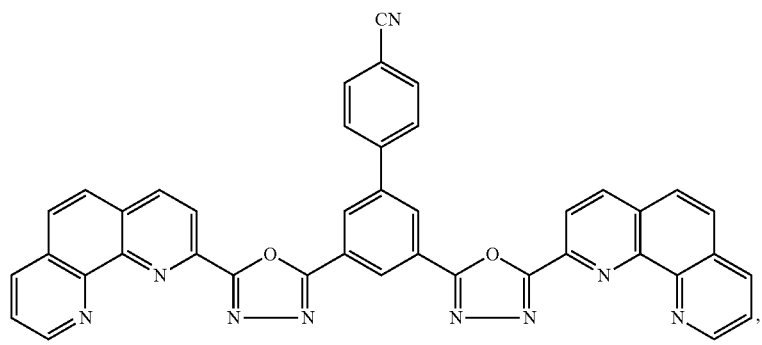

-continued
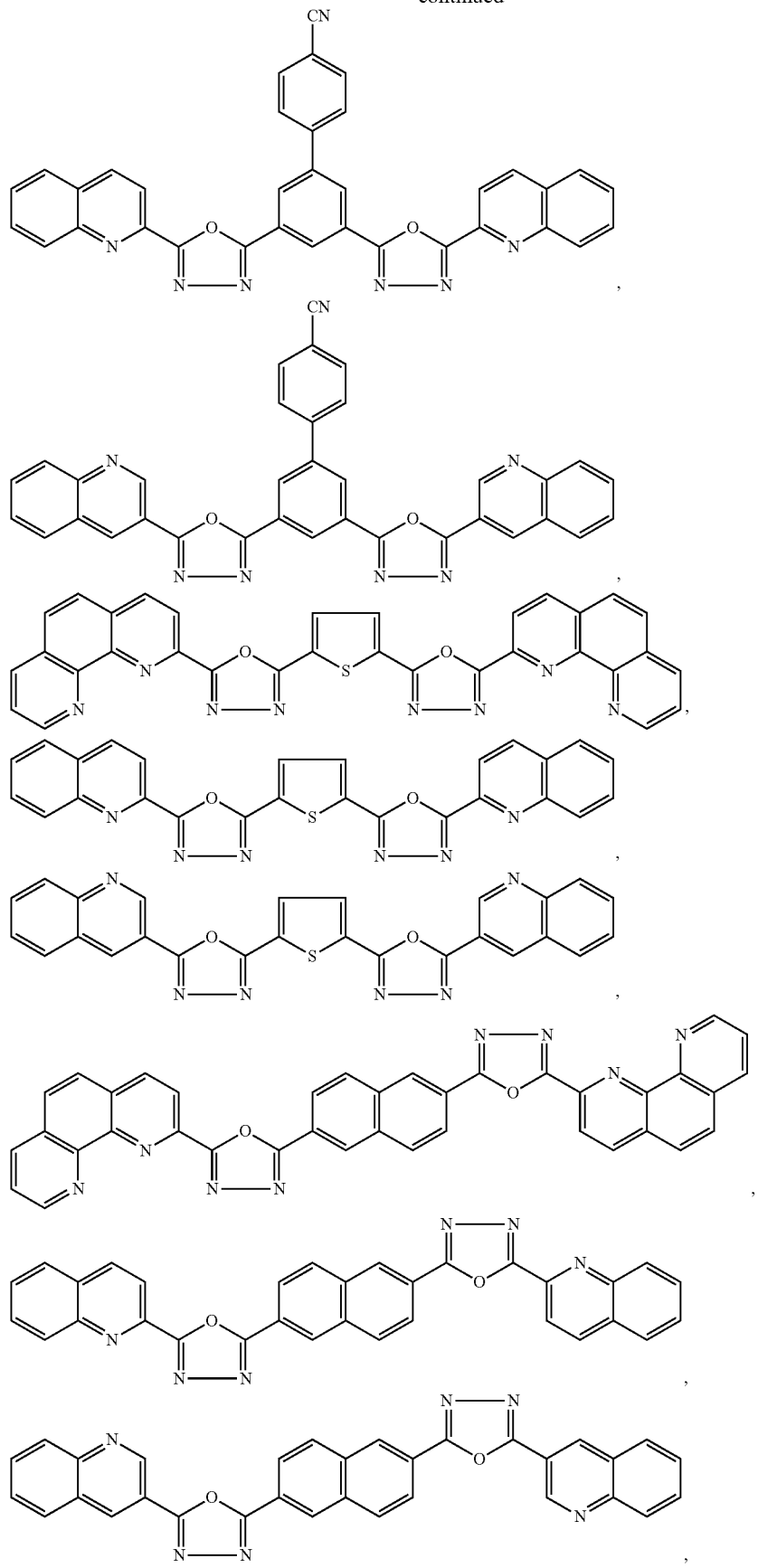

-continued
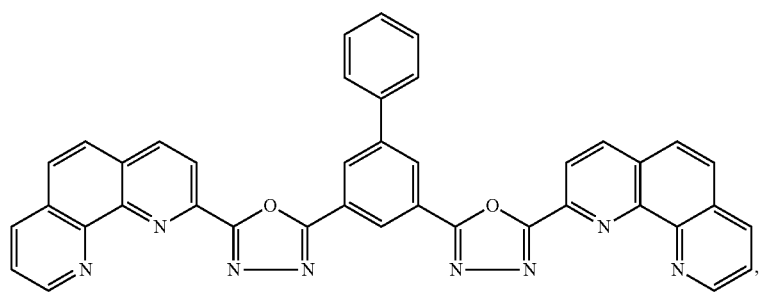
,
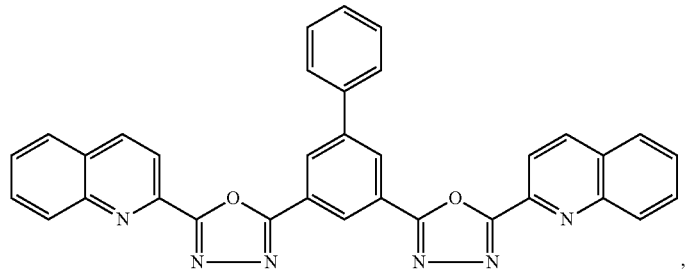
,
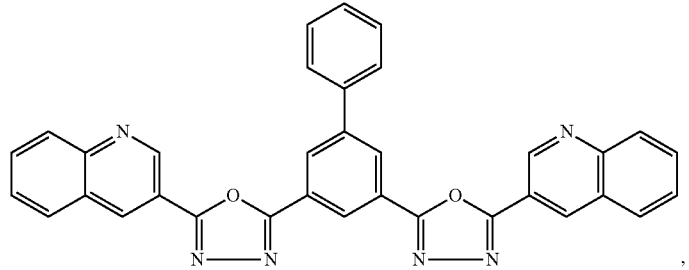
,
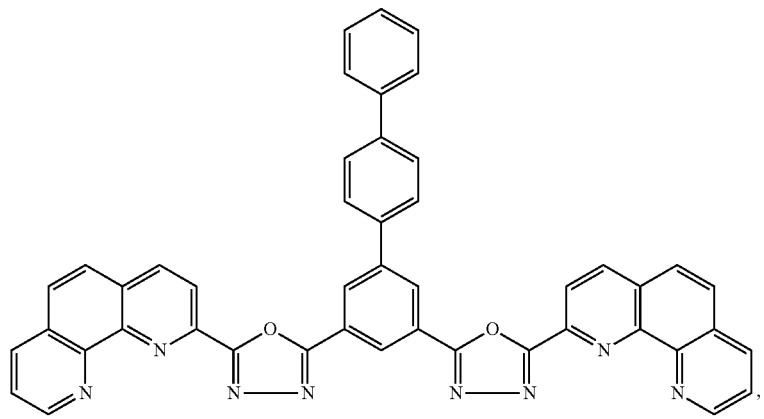
,
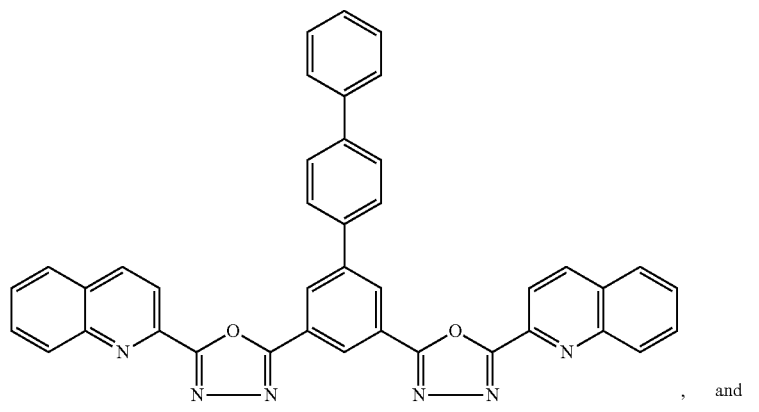
, and -continued

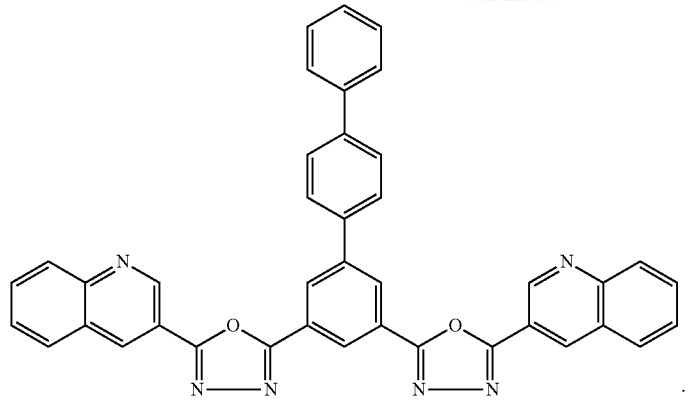

12. An organic electroluminescence device comprising a pair of electrodes and at least one organic layer sandwiched between the pair of electrodes, comprising, in the at least one organic layer, a compound according to claim 11.

13. The organic electroluminescence device according to claim 12, wherein the organic layer comprising the compound represented by formula (1) is an electron transport layer.

14. The organic electroluminescence device according to claim 12, wherein the organic layer comprising the compound represented by formula (1) is a hole blocking layer.

15. The organic electroluminescence device according to claim 12, wherein the organic layer comprising the compound represented by formula (1) is an emitting layer.

16. The compound of claim 1, wherein Ar represents a substituted or unsubstituted aromatic hydrocarbon group, excluding a terphenyl group.

17. The compound of claim 1, wherein Ar represents a substituted or unsubstituted aromatic heterocyclic group.

18. The compound of claim 1, wherein Ar represents a substituted or unsubstituted condensed polycyclic aromatic group.

19. The compound of claim 1, wherein Ar represents the substituted aromatic hydrocarbon is substituted with at least one selected from the group consisting of a fluorine atom, a chlorine atom, a cyano group, a hydroxide group, a nitro group, an alkyl group, an amino group, a substituted amino group, a trifluoromethyl group, a phenyl group, a naphthyl group, an aralkyl group, a substituted phenyl group, a substituted naphthyl group, and an substituted aralkyl group.

20. The organic electroluminescence device according to claim 2, wherein Ar of the compound is the substituted aromatic hydrocarbon is substituted with at least one selected from the group consisting of a fluorine atom, a chlorine atom, a cyano group, a hydroxide group, a nitro group, an alkyl group, an amino group, a substituted amino group, a trifluoromethyl group, a phenyl group, a naphthyl group, an aralkyl group, a substituted phenyl group, a substituted naphthyl group, and an substituted aralkyl group.

* * * * *